United States Patent
Graham et al.

(10) Patent No.: US 9,561,178 B2
(45) Date of Patent: *Feb. 7, 2017

(54) CYCLOSPORIN COMPOSITIONS

(75) Inventors: Richard S. Graham, Irvine, CA (US); Walter L. Tien, Irvine, CA (US); Mayssa Attar, Placentia, CA (US); Rhett Schiffman, Laguna Beach, CA (US); Aileen Morgan, Rancho Santa Margarita, CA (US)

(73) Assignee: Allergan, Inc., Irvine, CA (US)

( * ) Notice: Subject to any disclaimer, the term of this patent is extended or adjusted under 35 U.S.C. 154(b) by 1279 days.

This patent is subject to a terminal disclaimer.

(21) Appl. No.: 11/781,095

(22) Filed: Jul. 20, 2007

(65) Prior Publication Data
US 2008/0039378 A1 Feb. 14, 2008

Related U.S. Application Data

(60) Provisional application No. 60/820,239, filed on Jul. 25, 2006, provisional application No. 60/829,796, filed on Oct. 17, 2006, provisional application No. 60/829,808, filed on Oct. 17, 2006, provisional application No. 60/883,525, filed on Jan. 5, 2007, provisional application No. 60/916,352, filed on May 7, 2007, provisional application No. 60/869,459, filed on Dec. 11, 2006.

(51) Int. Cl.
| | |
|---|---|
| *A61K 38/13* | (2006.01) |
| *A61K 9/00* | (2006.01) |
| *A61K 47/02* | (2006.01) |
| *A61K 47/10* | (2006.01) |
| *A61K 47/26* | (2006.01) |
| *A61K 47/32* | (2006.01) |
| *A61K 47/44* | (2006.01) |

(52) U.S. Cl.
CPC ............ *A61K 9/0048* (2013.01); *A61K 38/13* (2013.01); *A61K 47/02* (2013.01); *A61K 47/10* (2013.01); *A61K 47/26* (2013.01); *A61K 47/32* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 5,051,402 A | | 9/1991 | Kurihara et al. |
| 5,294,604 A | | 3/1994 | Nussenblatt et al. |
| 5,474,979 A | * | 12/1995 | Ding et al. ............ 514/20.5 |
| 5,540,931 A | | 7/1996 | Hewitt et al. |
| 5,565,302 A | * | 10/1996 | Samukawa ............ G03F 7/033 430/281.1 |
| 5,951,971 A | | 9/1999 | Kawashima et al. |
| 6,008,192 A | | 12/1999 | Al-Razzak et al. |
| 6,562,873 B2 | * | 5/2003 | Olejnik et al. ............ 514/772.4 |
| 6,582,718 B2 | | 6/2003 | Kawashima et al. |
| 6,656,460 B2 | | 12/2003 | Benita et al. |
| 6,677,304 B2 | | 1/2004 | Di Napoli |
| 6,953,776 B2 | | 10/2005 | Di Napoli |
| 2001/0041671 A1 | | 11/2001 | Napoli |
| 2002/0045601 A1 | | 4/2002 | Kawashima et al. |
| 2004/0092435 A1 | | 5/2004 | Peyman |
| 2004/0106546 A1 | | 6/2004 | Napoli |
| 2005/0059583 A1 | * | 3/2005 | Acheampong et al. ........ 514/11 |
| 2005/0106189 A1 | | 5/2005 | Wohlrab et al. |
| 2005/0277584 A1 | | 12/2005 | Tien et al. |
| 2006/0148686 A1 | | 7/2006 | Xia et al. |
| 2009/0131307 A1 | * | 5/2009 | Tien et al. ...................... 514/11 |

FOREIGN PATENT DOCUMENTS

| | | |
|---|---|---|
| WO | WO 02-49603 A | 6/2002 |
| WO | WO 2006-050837 A | 5/2006 |
| WO | WO 2007-008894 A | 1/2007 |
| WO | WO 2007/011880 | 1/2007 |
| WO | WO 2007/056457 | 5/2007 |
| WO | WO 2008/014200 * | 1/2008 |

OTHER PUBLICATIONS

Kanai et al ('The effect of the cornea of alpha cyclodextrin vehicle for cyclosporine eye drops' Transplantation Proceedings 1989 v21 pp. 3150-3152).*

IUPAC Goldbook (retrieved from http://goldbook.iupac.org/S05746.html on Oct. 8, 2015, 1 page).*

Encyclopedia Britannica (retrieved from http://www.britannica.com/science/emulsion-chemistry on Oct. 5, 2015, 2 pages).*

Reynolds et al, "Therapeutic option for the management of early neurotrophic keratopathy: A case report and review", Journal of the American Optometric Association, vol. 77. No. 10, pp. 503-507, 2006.

Acheampong, Andrew, et al., "Cyclosporine Distribution into the Conjunctiva, Cornea, Lacrimal Gland, and Systemic Blood Following Topical Dosing of Cyclosporine to Rabbit, Dog, and Human Eyes" Adv Exp Med Biol 1998; 438:1001-4.

Small, Dave, et al., "The Ocular Pharmacokinetics of Cyclosporine in Albino Rabbits and Beagle Dogs" Assoc. Ocular Pharm Ther 1999; 54.

Tesavibul, N., et al., "Topical Cyclosporine A (CsA) for Ocular Surface Abnormalities in Graft Versus Host Disease Patients" Invest Ophthalmol Vis Sci Feb. 1996; 37(3):S1026.

Ding, Shulin, et al., "Cyclosporine Ophthalmic O/W EMulsion: Formulation and Emulsion Characterization" AN98040585, Pharm Res 1997; 14 (11 Suppl):S41.

Lyons, R. T., et al., "Influence of Three Emulsion Formulation Parameters on the Ocular Bioavailability of Cyclosporine A in Albino Rabbits" Am Assoc Pharm Sci 2000;2(4):1 page.

Angelov, O., et al., "Safety Assessment of Cyclosporine Ophthalmic Emulsion in Rabbits and Dogs" AN98071079, Soc Ophthalmol Eur 1997; 25-28.

Kanpolat, Ayfer, et al., "Penetration of Cyclosporin A Into the Rabbit Cornea and Aqueous Humor After Topical Drop and COllagen Shield Administration" The CLAO Journal, Apr. 1994, vol. 20, No. 2, pp. 119-122.

(Continued)

Primary Examiner — Karlheinz R Skowronek
Assistant Examiner — Ronald Niebauer
(74) Attorney, Agent, or Firm — Laura L. Wine

(57) ABSTRACT

Disclosed herein are therapeutic methods, compositions, and medicaments related to cyclosporine.

10 Claims, 5 Drawing Sheets

(56) References Cited

OTHER PUBLICATIONS

Hiroyuki, Kawano, et al., "Effectiveness of Hydrophilic Cyclosporin Eye Drops for Penetrating Keratoplasty on Albino Rabbits" Abstract SciFinder, May 26, 2006, p. 2.
Rubin, Michael, et al., "Efficacy of Topical Cyclosporin 0.05% in the Treatment of Posterior Blepharitis" Journal of Ocular Pharmacology and Therapeutics, vol. 22, No. 1, 2006, pp. 47-53.
Kanai, A., et al., "The Effect on the Cornea of Alpha Cyclodextrin Vehicle for Cyclosporin Eye Drops" Transplantation Proceedings, vol. 21, No. 1, Feb. 1989, pp. 3150-3152.
Abdulrazik, M., et al., "Ocular Delivery of Cyclosporin A II. Effect of Submicron Emulsion's Surface Charge on Ocular Distribution of Topical Cyclosporin A" STP Pharma Sciences II (6), 2001, pp. 427-432.
Cheeks, Lisa, et al., "Influence of Vehcile and Anterior Chamber Protein Concentration on Cyclosporine Penetration Through the Isolated Rabbit Cornea" Current Eye Research, vol. 11, No. 7, 1992, pp. 641-649.
Acheampong, Andrew A., et al., "Distribution of Cyclosporin A in Ocular Tissues After Topical Administration to Albino Rabbits and Beagle Dogs" Current Eye Research, vol. 18, No. 2, 1999, pp. 91-103.
Quintana-Hau, et al., "In Vitro Study of Corneal Retention of Cyclosporine-A from Different Formulations" Invest Ophthalmol Vis Sci, 2004; 45: E-Abstract 67.
Rao, S.N., "Comparison of the Efficacy of Topical Cyclosporine 0.05% Compared With Tobradex for the Treatment of Posterior Blepharitis" Invest Ophthalmol Vis Sci 2005; 46: E-Abstract 2662.
Mizutani, Hideki, et al., "Investigation of Pharmaceutical Characteristics of Cyclosporin A Aqueous Eye Drops and Their Topical Application in Clinical Practice" JPN J. Pharm. Health Care Sci., 2005, 31(7):563-566.
Lallemand, F., et al., "Cyclosporin A Delivery to the Eye: A Pharmaceutical Challenge" Eur J Pharm Biophann, Nov. 2003, 56 (3), pp. 307-318.
Tatlipinar, S., et al., "Topical Ciclosporin in the Treatment of Ocular Surface Disorders" Br J Ophthalmol, 2005, 89(10), pp. 1363-7.
Kuwano, Mitsuaki, et al., "Cyclosporine A Formulation Affects Its Ocular Distribution in Rabbits" Pharmaceutical Research, 2002, vol. 19, No. 1, pp. 108-111.

\* cited by examiner

CYCLOSPORIN COMPOSITIONS

RELATED APPLICATION

This application is based, and claims priority under 35 U.S.C. §120 to U.S. Provisional Application Ser. No. 60/820,239, filed Jul. 25, 2006; U.S. Provisional Application Ser. No. 60/829,796, filed Oct. 17, 2006; U.S. Provisional Application Ser. No. 60/829,808, filed Oct. 17, 2006; U.S. Provisional Application Ser. No. 60/883,525, filed Jan. 5, 2007; U.S. Provisional Application Ser. No. 60/916,352, filed May 7, 2007; and U.S. Provisional Application Ser. No. 60/869,459, filed Dec. 11, 2006; each of which is hereby incorporated by reference in their entirety.

BACKGROUND OF THE INVENTION

Abnormalities associated with the function of the lacrimal gland or with tearing often cause discomfort to mammals who suffer from these abnormalities.

DETAILED DESCRIPTION OF THE INVENTION

Figure 1:
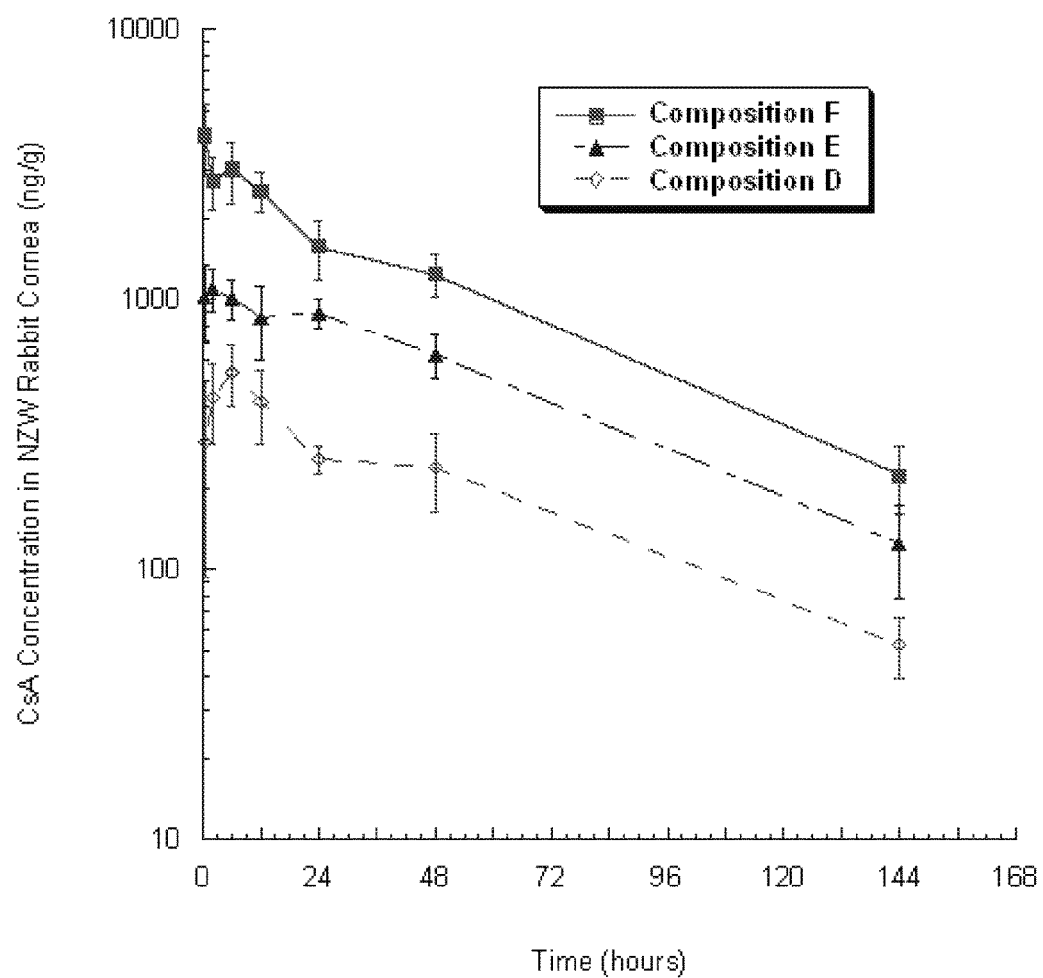
FIG. 1 Mean (±SD) cornea cyclosporine A concentrations (semi-log) following a single bilateral topical ocular instillation of one of three 0.05% cyclosporine A formulations to New Zealand White rabbits.

A composition comprising cyclosporin A at a concentration of from about 0.0001% (w/v) to less than about 0.05% (w/v) is disclosed herein.

We have surprisingly discovered that compositions of cyclosporin A at a concentration of less than about 0.05% (w/v) can be prepared that will be therapeutically effective.

In one embodiment, the compositions disclosed herein are administered to an eye of a mammal in need thereof to enhance or restore lacrimal gland tearing.

In another embodiment, the compositions disclosed herein are administered to an eye of a mammal in need thereof to increase tear production in a tear-deficient eye.

In another embodiment, the compositions disclosed herein are administered to an eye of a mammal in need thereof to treat keratoconjunctivitis sicca.

In another embodiment, the compositions disclosed herein are administered to an eye of a mammal in need thereof to treat dry eye disease.

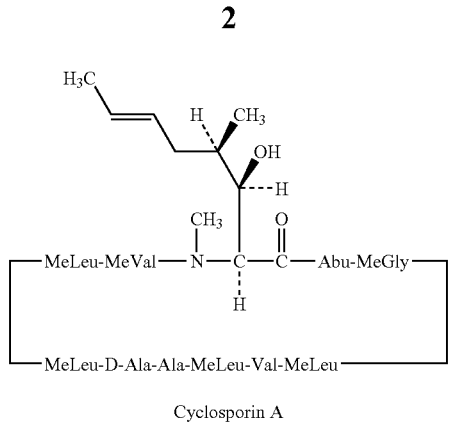

Cyclosporin A

Cyclosporin A is a cyclic peptide with immunosuppressive properties having the structure shown above. It is also known by other names including cyclosporine, cyclosporine A, ciclosporin, and ciclosporin A.

Treatment Methods

One embodiment is a method of treating dry eye disease comprising topically administering to a mammal in need thereof a composition comprising cyclosporin A at a concentration of from 0.0001% (w/v) to less than about 0.05% (w/v).

The treatment generally comprises administering 10-50 μL drops of the compositions disclosed herein topically to the eye or eyes of the mammal or human. Determination of the number of drops administered per day to the person or mammal to provide effective relief is within the skill of the ordinary artisan.

In one embodiment, the composition is administered from 1 to 4 times per day.

In another embodiment, the composition is administered twice a day.

In another embodiment, the composition is administered only once a day.

In another embodiment, less than 14% of patients suffer ocular burning when the composition is administered only once a day for a period of three months.

In another embodiment, less than 10% of patients suffer ocular burning when the composition is administered only once a day for a period of three months.

In another embodiment, less than 8% of patients suffer ocular burning when the composition is administered only once a day for a period of three months.

For the purposes of this disclosure, "treat," "treating," or "treatment" refer to the use of a compound, composition, therapeutically active agent, or drug in the diagnosis, cure, mitigation, treatment, prevention of disease or other undesirable condition, or to affect the structure or any function of the body of man or other animals.

Compositions

The concentration of cyclosporin A is less than about 0.05%. This is intended to mean that the concentration is lower than the concentration in the commercially available 0.05% cyclosporin A emulsion known as Restasis®.

In another embodiment, the concentration of cyclosporin A is from about 0.005% (w/v) to about 0.04% (w/v).

In another embodiment, the concentration of cyclosporin A is from about 0.02% (w/v) to about 0.04% (w/v).

In another embodiment, the concentration of cyclosporine A is about 0.005% (w/v).

In another embodiment, the concentration of cyclosporine A is about 0.015% (w/v).

In another embodiment, the concentration of cyclosporine A is about 0.02% (w/v).

In another embodiment, the concentration of cyclosporine A is about 0.03% (w/v).

In another embodiment, the concentration of cyclosporine A is about 0.04% (w/v).

A liquid which is ophthalmically acceptable is formulated such that it can be administered topically to the eye. The comfort should be maximized as much as practicable, although sometimes formulation considerations (e.g. drug stability, bioavailability, etc.) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions are often maintained at a comfortable pH with an appropriate buffer system. The formulations may also contain conventional, pharmaceutically acceptable preservatives, stabilizers and surfactants.

Various buffers and means for adjusting pH may be used so long as the resulting preparation is ophthalmically acceptable. Accordingly, buffers include, but are not limited to, acetate buffers, citrate buffers, phosphate buffers and borate buffers. Acids or bases may be used to adjust the pH of these formulations as needed.

In another embodiment, the composition contains a preservative.

Preservatives that may be used in the pharmaceutical compositions disclosed herein include, but are not limited to, cationic preservatives such as
quaternary ammonium compounds including benzalkonium chloride, polyquad, and the like;
guanidine-based preservatives including PHMB, chlorhexidine, and the like;
chlorobutanol;
mercury preservatives such as thimerosal, phenylmercuric acetate and phenylmercuric nitrate; and
oxidizing preservatives such as stabilized oxychloro complexes (e.g. Purite®).

In another embodiment, the composition contains a surfactant.

A surfactant may be used for assisting in dissolving an excipient or an active agent, dispersing a solid or liquid in a composition, enhancing wetting, modifying drop size, or a number of other purposes. Useful surfactants include, but are not limited to surfactants of the following classes: alcohols; amine oxides; block polymers; carboxylated alcohol or alkylphenol ethoxylates; carboxylic acids/fatty acids; ethoxylated alcohols; ethoxylated alkylphenols; ethoxylated aryl phenols; ethoxylated fatty acids; ethoxylated; fatty esters or oils (animal & veg.); fatty esters; fatty acid methyl ester ethoxylates; glycerol esters; glycol esters; lanolin-based derivatives; lecithin and lecithin derivatives; lignin and lignin derivatives; methyl esters; monoglycerides and derivatives; polyethylene glycols; polymeric surfactants; propoxylated & ethoxylated fatty acids, alcohols, or alkyl phenols; protein-based surfactants; sarcosine derivatives; sorbitan derivatives; sucrose and glucose esters and derivatives.

In particular, ethoxylate surfactants are useful.

An ethoxylate surfactants is one that comprises the moiety —O(CH$_2$CH$_2$O)$_n$—OH, wherein n is at least about 1.

In one embodiment n is from about 1 to about 10,000.

In another embodiment, n is from 1 to about 1000.

In another embodiment, n is from about 1 to about 500.

Some ethoxylates contain one ethoxylate moiety. In other words, there is a single ethoxylate chain on each molecule.

Examples of surfactants with one ethoxylate moiety, include, but are not limited to:

Ethoxylated alcohols wherein the alcohol has a single hydroxyl unit; alkylphenol ethoxylates; ethoxylated fatty acids; fatty acid methyl ester ethoxylates; polyethylene glycols; and the like.

Ethoxylates may comprise more than one ethoxylate moiety. In other words, there may be ethoxylate moieties attached to several different parts of the molecule. Examples include, but are not limited to: block polymers; ethoxylated oils; sorbitan derivatives; sucrose and glucose ethoxylates; and the like.

Block Polymers: These are polymers with the structure A-B-A', wherein A and A' are polyethylene chains of 1 or more ethylene units, and B is a polypropylene chain of one or more propylene units. Generally, but not necessarily, A and A' are approximately the same length.

In one embodiment, A and A' contain from about 2 to about 200 ethylene units.

In another embodiment, A and A' contain from about 5 to about 100 ethylene units.

In another embodiment, A and A' contain about 7 to about 15 ethylene units.

In another embodiment, A and A' contain about 7, about 8, or about 12 ethylene units.

In another embodiment, B contains from about 25 to about 100 propylene units.

In another embodiment, B contains from about 30 to about 55 propylene units.

In another embodiment, B contains about 30, about 34, or about 54 propylene units.

In another embodiment, the molecular weight is from about 1000 to about 20000.

In another embodiment, the molecular weight is from about 2000 to about 10000.

In another embodiment, the molecular weight is about 2500, about 3000, about 3800, or about 8400.

These include but are not limited to:

Poloxalene: wherein A has about 12 ethylene oxide units, B has about 34 propylene oxide units, A' has about 12 ethylene oxide units, and the average molecular weight is about 3000.

Poloxamer 182: wherein A has about 8 ethylene oxide units, B has about 30 propylene oxide units, A' has about 8 ethylene oxide units, and the average molecular weight is about 2500

Poloxamer 188: wherein A has about 75 ethylene oxide units, B has about 30 propylene oxide units, A' has about 75 ethylene oxide units, and the average molecular weight is about 8400.

Poloxamer 331: wherein A has about 7 ethylene oxide units, B has about 54 propylene oxide units, A' has about 7 ethylene oxide units, and the average molecular weight is about 3800;

Ethoxylated Alcohols

These include but are not limited to:

Ethoxylates of linear alcohols having from about 6 to about 20 carbon atoms.

In one embodiment, the linear alcohol has from about 10 to about 16 carbon atoms.

In another embodiment, n is from about 1 to about 100.

In another embodiment, n is from about 1 to about 50.

In another embodiment, n is from about 5 to about 50 ethylene oxide units.

In another embodiment, n is from about 1 to about 20 ethylene oxide units.
In another embodiment, n is from about 30 to about 50 ethylene oxide units.
Ethoxylated Alkylphenols
These are alkylphenols that are ethoxylated, i.e. the phenolic OH is replaced with an ethoxylate moiety.
These include but are not limited to:
octylphenol ethoxylate, i.e. $CH_{17}Ph(OCH_2CH_2O)_nH$.
nonylphenol ethoxylate, i.e. $CH_{19}Ph(OCH_2CH_2O)_nH$.
alkyphenols of the above formula wherein n is from about 1 to about 100.
alkyphenols of the above formula wherein n is from about 1 to about 50.
alkyphenols of the above formula wherein n is from about 9 to about 15.

Octyl Phenol 1.5 Mole Ethoxylate (i.e. n is an average of about 1.5); Octyl Phenol 5 Mole Ethoxylate; Octyl Phenol 7 Mole Ethoxylate; Octyl Phenol 9 Mole Ethoxylate; Octyl Phenol 12 Mole Ethoxylate; Octyl Phenol 40 Mole Ethoxylate; Nonyl Phenol 1.5 Mole Ethoxylate; Nonyl Phenol 4 Mole Ethoxylate; Nonyl Phenol 6 Mole Ethoxylate; Nonyl Phenol 9 Mole Ethoxylate; Nonyl Phenol 10 Mole Ethoxylate; Nonyl Phenol 10.5 Mole Ethoxylate; Nonyl Phenol 12 Mole Ethoxylate; Nonyl Phenol 15 Mole Ethoxylate; Nonyl Phenol 15 Mole Ethoxylate; Nonyl Phenol 30 Mole Ethoxylate; and Nonyl Phenol 40 Mole Ethoxylate; Ethoxylated Fatty Acids,
These include but are not limited to:
ethoxylates which are esterified to form either:
    monoesters, i.e. $RCO_2(CH_2CH_2O)_nOH$, where $RCO_2H$ is a fatty acid; or
    diesters, i.e. $RCO_2(CH_2CH_2O)_nC(=O)R$.
Fatty acids include, but are not limited to:
Saturated fatty acids, which have no C=C moieties and include myristic acid, palmitic acid, stearic acid, arachidic acid, behenic acid, lignoceric acid.
Unsaturated fatty acids, including the following:
    monounsaturated fatty acids, which have one C=C group such as palmitoleic acid, oleic acid, and nervonic acid;
    diunsaturated fatty acids, which have two C=C groups, such as linoleic acid;
    triunsaturated fatty acids, which have three C=C groups, such as α-linolenic acid and γ-linolenic acid;
    tetraunsaturated fatty acids, which have four C=C groups, such as arachidonic acid; and
    pentaunsaturated fatty acids, which have five C=C groups, such as eicosapentaenoic acid.
The following may also be used:
Lauric Acid; 14 carbon fatty acids such as myristic acid; 16 carbon fatty acids such as palmitic and palmitoleic acid; 18 carbon fatty acids such as stearic acid, oleic acid, linoleic acid, α-linolenic acid, and γ-linolenic acid; 20 carbon fatty acids such as eicosapentaenoic acid; 22 carbon fatty acids such as arachidic acid; and 24 carbon fatty acids such as lignoceric acid and nervonic acid.
In one embodiment, n is from about 2 to about 100.
In another embodiment, n is from about 5 to about 50.
In another embodiment, n is from about 30 to 50.
Ethoxylated Fatty Esters or Oils (Animal & Veg.).
These are the products which result from reacting ethylene oxide with a fatty ester or an oil. When a fatty oil is used, the products is a mixture of ethoxylates of the fatty acids present in the oil, ethoxylates of glycerine, ethoxylates of mono and diglycerides, and the like.
Specific examples include, but are not limited to:
Ethoxylates of the following oils: Anise oil, Castor oil, Clove oil, Cassia oil, Cinnamon oil; Almond oil, Corn oil, Arachis oil, Cottonseed oil, Safflower oil, Maize oil, Linseed oil, Rapeseed oil, Soybean oil, Olive oil, Caraway oil, Rosemary oil, Peanut oil, Peppermint oil, Sunflower oil, Eucalyptus oil and Sesame oil; Coriander oil, Lavender oil, Citronella oil, Juniper oil, Lemon oil, Orange oil, Clary sage oil, Nutmeg oil, Tea tree oil, coconut oil, tallow oil, and lard;
In one embodiment, from 1 to about 50 moles of ethylene oxide is used per mole of the oil triglyceride.
In another embodiment, from about 30 to about 40 moles of ethylene oxide is used per mole of the oil triglyceride.
Ethylene oxide may also react with a fatty acid ester with a formula $RCO_2R'$ to form $RCO_2(CH_2CH_2O)_nR'$. Thus, surfactants having the formula $RCO_2(CH_2CH_2O)_nR'$, where $RCO_2H$ is a fatty acid and R' is alkyl having from 1 to 6 carbons are contemplated.
One embodiment is a fatty acid methyl ester ethoxylate, wherein R' is methyl.
In another embodiment, $RCO_2H$ is Lauric Acid; a 14 carbon fatty acid such as myristic acid; a 16 carbon fatty acid such as palmitic and palmitoleic acid; an 18 carbon fatty acids such as stearic acid, oleic acid, linoleic acid, α-linolenic acid, and γ-linolenic acid; a 20 carbon fatty acids such as eicosapentaenoic acid; a 22 carbon fatty acids such as arachidic acid; or a 24 carbon fatty acids such as lignoceric acid and nervonic acid.
Polyethylene Glycols are ethoxylates that are unsubstituted, or terminated with oxygen on both ends, i.e. $HO(CH_2CH_2O)_nH$,
Sorbitan Derivatives:
These are ethoxylated sorbates having a fatty acid capping one or more of the ethoxylated chains. For example, polysorbate 80 has an oleate cap as shown in the structure below.

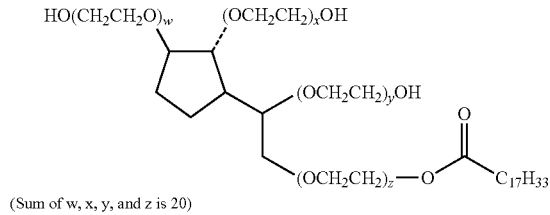

Polysorbate 80

(Sum of w, x, y, and z is 20)

These compounds are named as POE (w+x+y+z) sorbitan mono (or di- or tri-) fatty acid.
For example, Polysorbate 80 is POE (20) sorbitan monooleate. Thus, the number in parenthesis is the total number of ethylene oxide units on the molecule, and the ending is the number of acid caps and the capping acid.
These include but are not limited to:
Sorbitan derivatives wherein the total number of ethylene oxide units is from 3 to 30;
Sorbitan derivatives wherein the total number of ethylene oxide units is 4, 5, or 20;
Sorbitan derivatives wherein the capping acid is laurate, palmitate, stearate, or oleate;
The sorbitan derivative may be a POE sorbitan monolaurate;
a POE sorbitan dilaurate;
a POE sorbitan trilaurate;
a POE sorbitan monopalmitate;
a POE sorbitan dipalmitate;
a POE sorbitan tripalmitate;

a POE sorbitan monostearate;
a POE sorbitan distearate;
a POE sorbitan tristearate;
a POE sorbitan monooleate;
a POE sorbitan dioleate;
or a POE sorbitan trioleate;
Specific examples include:
POE (20) sorbitan monolaurate; POE (4) sorbitan monolaurate; POE (20) sorbitan monopalmitate; POE (20) monostearate; POE (20) sorbitan monostearate; POE (4) sorbitan monostearate; POE (20) sorbitan tristearate; POE (20) sorbitan monoleate; POE (20) sorbitan 15 monoleate; POE (5) sorbitan 10 monoleate; POE (20) sorbitan trioleate; and
Sucrose and Glucose Esters and Derivatives:
Although there are a number of sucrose and glucose based surfactants, some sucrose and glucose esters and derivatives are similar to the sorbate derivatives described above. In other words, one, several, or all of the hydroxyl moieties of the sugar are ethoxylated, and one or more of the ethoxylate chains are capped with a carboxylic acid. Other sucrose and glucose esters are simply ethoxylated, but do not have a capping carboxylic acid. Other sucrose and glucose esters may be ethoxylated and capped with an alkyl group formed by reaction with an alcohol. Other sucrose and glucose esters may be esters or ethers of the sugars with hydrophobic chains and have ethoxylates substituted in other positions on the sugar.

Various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose, and acrylates (e.g. Pemulen®).

Tonicity adjustors may be added as needed or convenient. They include, but are not limited to, salts, particularly sodium chloride, potassium chloride, mannitol and glycerin, or any other suitable ophthalmically acceptable tonicity adjustor.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

Compositions may be aqueous solutions or emulsions, or some other acceptable liquid form. For an emulsion, one or more oils will be used to form the emulsion, and in some instances one or more surfactants will be required. Suitable oils include, but are not limited to anise oil, castor oil, clove oil, cassia oil, cinnamon oil, almond oil, corn oil, arachis oil, cottonseed oil, safflower oil, maize oil, linseed oil, rapeseed oil, soybean oil, olive oil, caraway oil, rosemary oil, peanut oil, peppermint oil, sunflower oil, eucalyptus oil, sesame oil, and the like.

In one embodiment, the composition is an aqueous solution.

In another embodiment, the composition contains no ethanol.

In another embodiment, the composition contains no hyauronic acid.

In another embodiment, the composition contains no vitamin E TPGS.

In another embodiment, the composition contains no cyclodextrin A.

In another embodiment, the composition contains no cyclodextrin.

Example 1

| Ingredients | Percent Ingredients (% w/v) | Amount needed (g) for a 1 liter batch |
| --- | --- | --- |
| Cyclosporine | 0% for Placebo (P) | 0 grams for Placebo (P) |
|  | 0.03% (A) | 0.30 (A) |
|  | 0.04% (B) | 0.40 (B) |
|  | 0.05% (C) | 0.5 (C) |
| Carboxymethylcellulose sodium | 0.5 | 5.0 |
| Polysorbate 80 | 1.0 | 10.0 |
| Glycerin | 1.0 | 10.0 |
| Mannitol | 0.5 | 5.0 |
| Sodium Citrate Dihydrate | 0.4 | 4.0 |
| Boric Acid | 0.25 | 2.5 |
| Sodium Borate Decahydrate | 0.41 | 4.1 |
| Potassium Chloride | 0.14 | 1.4 |
| Purite | 0.01 | 0.1 |
| Purified Water | q.s. to 100% | q.s to 100% |

Compositions P, A, B and C, are prepared according to the following procedure.
1. Measure Purified Water to about 90% of the batch size and place in an appropriate beaker or container.
2. Begin mixing the water with a strong mixer (Rotosolver) to obtain a strong vortex.
3. Add the pre-weighed carboxymethylcellulose sodium into the strong vortex. Continue strong mixing for at least 1 hour.
4. Slow mixer to a slow speed.
5. Add and dissolve the pre-weighed polysorbate 80.
6. Add and dissolve the pre-weighed glycerin.
7. Add and dissolve the pre-weighed mannitol.
8. Add and dissolve the pre-weighed sodium citrate dehydrate.
9. Add and dissolve the pre-weighed boric acid.
10. Add and dissolve the pre-weighed sodium borate decahydrate.
11. Add and dissolve the pre-weighed potassium chloride.
12. Check pH and adjust if necessary. Target pH is 7.5+/−0.1.
13. Add and dissolve the pre-weighed Purite.
14. Add sufficient quantity of Purified Water to attain the final batch volume. This will provide the finished placebo formulation (P).
Procedure for Either 0.03% (A), 0.04% (B), 0.05% (C)
15. Measure the exact amount of Placebo (9815×) needed to satisfy the batch size requirements and place in a media bottle that contains a magnetic stir bar.
16. Add and dissolve the pre-weighed cyclosporine. Stir at a slow speed to avoid foaming. It will usually take overnight mixing to completely dissolve the cyclosporine.
17. After overnight mixing is completed, pump the cyclosporine solution through a Millipore Milligard pre-filter and a Pall Suporlife sterilizing filter and collect the filtrate aseptically.
18. The sterile filtrate can then be aseptically dispensed into multidose dropper bottles suitable for ophthalmic purpose.
19. The finished product should be tested for cyclosporine assay, pH, osmolality, viscosity, Purite, sterility, and antimicrobial effectiveness.
20. The finished product should be store at room temperature and protected from light.

Example 2

The following formulations were prepared. D and E were prepared by standard methods known in the art. F was prepared as described above for A-C except that Pemulen TR-2 was substituted for carboxymethylcellulose sodium, and the addition of the citrate and borate buffers were omitted.

|  | D Emulsion | E Emulsion | F Solution |
|---|---|---|---|
| Cyclosporin A | 0.05 | 0.05 | 0.05 |
| Castor Oil | 1.25 | 0.30 | N/A |
| Polyoxyethylene 40 Stearate, NF | N/A | 0.30 | N/A |
| Polysorbate 80 | 1.00 | 0.30 | 1.00 |
| Glycerin | 2.20 | 1.00 | 1.00 |
| Mannitol | N/A | 2.00 | 2.00 |
| Pemulen TR-2 | 0.05 | 0.10 | 0.10 |
| Sodium Hydroxide (1N) | pH adjustment | pH adjustment | pH adjustment |
| Purified Water | QS | QS | QS |
| pH | pH = 7.4 | 7.39 | 7.35 |

Bioavailability

The compositions disclosed and used herein provide a therapeutically effective amount of cyclosporin A to a mammal. However, while not intending to limit the scope of the invention in any way, concentrations of cyclosporin A in the compositions may be significantly lower than those normally associated with a therapeutically effective concentration. For example, one commercial preparation, marketed as Restasis® by Allergan, Inc., is a 0.05% cyclosporin A castor oil emulsion. Other compositions currently in development have concentrations of 0.1% or higher.

Reported herein are pharmacokinetic data for in vivo experiments on rabbits. However, the rabbit experiments are believed to be useful models for bioavailability in other mammals including humans. Thus, although bioavailability parameters are disclosed and featured in the claims, they should not be construed as limiting the treatment to rabbits only, but the compositions characterized and defined by bioavailability in rabbits are also contemplated for use in treatment in other mammals, particularly humans.

In one embodiment, the composition provides more cyclosporin A to the cornea of a person than Composition AA.

In another embodiment, the composition provides more cyclosporin A to the cornea of a person than Composition BB.

In another embodiment, the composition provides more cyclosporin A to the cornea of a person than Composition CC.

In one embodiment, the composition provides more cyclosporin A to the cornea of a person than Composition DD.

In another embodiment, the composition provides more cyclosporin A to the cornea of a person than Composition EE.

In another embodiment, the composition provides more cyclosporin A to the cornea of a person than Composition FF.

In one embodiment, the composition provides more cyclosporin A to the cornea of a person than Composition GG.

In another embodiment, the composition provides more cyclosporin A to the cornea of a person than Composition HH.

In another embodiment, the composition provides more cyclosporin A to the cornea of a person than Composition II.

In another embodiment, the composition provides more cyclosporin A to the cornea of a person than Composition JJ.

In another embodiment, the composition provides more cyclosporin A to the cornea of a person than Composition KK.

In another embodiment, the composition provides more cyclosporin A to the cornea of a person than Composition LL.

In another embodiment, the composition provides more cyclosporin A to the cornea of a person than Composition MM.

In one embodiment, the composition provides more cyclosporin A to the conjunctiva of a person than Composition AA.

In another embodiment, the composition provides more cyclosporin A to the conjunctiva of a person than Composition BB.

In another embodiment, the composition provides more cyclosporin A to the conjunctiva of a person than Composition CC.

In one embodiment, the composition provides more cyclosporin A to the conjunctiva of a person than Composition DD.

In another embodiment, the composition provides more cyclosporin A to the conjunctiva of a person than Composition EE.

In another embodiment, the composition provides more cyclosporin A to the conjunctiva of a person than Composition FF.

In one embodiment, the composition provides more cyclosporin A to the conjunctiva of a person than Composition GG.

In another embodiment, the composition provides more cyclosporin A to the conjunctiva of a person than Composition HH.

In another embodiment, the composition provides more cyclosporin A to the conjunctiva of a person than Composition II.

In another embodiment, the composition provides more cyclosporin A to the conjunctiva of a person than Composition JJ.

In another embodiment, the composition provides more cyclosporin A to the conjunctiva of a person than Composition KK.

In another embodiment, the composition provides more cyclosporin A to the conjunctiva of a person than Composition LL.

In another embodiment, the composition provides more cyclosporin A to the conjunctiva of a person than Composition MM.

In another embodiment, topical administration of one 35 μL drop of said composition to each eye of a female New Zealand white rabbit provides to the corneas of said rabbit at least about 500 ng of cyclosporin A per gram of cornea of said rabbit at 30 minutes after said topical administration.

In another embodiment, wherein topical administration of one 35 μL drop of said composition to each eye of a female New Zealand white rabbit provides to the corneas of said rabbit at least about 1000 ng of cyclosporin A per gram of cornea of said rabbit at 30 minutes after said topical administration.

In another embodiment, topical administration of one 35 μL drop of said composition to each eye of a female New Zealand white rabbit provides to the corneas of said rabbit at least about 1400 ng of cyclosporin A per gram of cornea of said rabbit at 30 minutes after said topical administration.

In another embodiment, wherein topical administration of one 35 µL drop of said composition to each eye of a female New Zealand white rabbit provides to the corneas of said rabbit at least about 2000 ng of cyclosporin A per gram of cornea of said rabbit at 30 minutes after said topical administration.

In another embodiment, topical administration of one 35 µL drop of said composition to each eye of a female New Zealand white rabbit provides to the corneas of said rabbit at least about 2400 ng of cyclosporin A per gram of cornea of said rabbit at 30 minutes after said topical administration.

In another embodiment, topical administration of one 35 µL drop of said composition to each eye of a female New Zealand white rabbit provides to the corneas of said rabbit at least about 17000 ng of cyclosporin A per gram of cornea of said rabbit over a period of 24 hours after said topical administration.

In another embodiment, said composition is an aqueous solution containing from 0.005% to about 0.04% cyclosporin A, wherein topical administration of one 35 µL drop of said composition to each eye of a New Zealand rabbit provides at least about 17000 ng of cyclosporin A per gram of cornea to the corneas of said rabbit as determined by:
  topically administering said composition to each eye of each of 15 female New Zealand white rabbit test subjects; and
  determining the amount of cyclosporin A in the corneas of three subjects at times of about 0.5 hours, about 2 hours, about 6 hours, about 12 hours, and about 24 after administration to said subject;
wherein the amount of cyclosporin A in the cornea is determined only once for each subject.

In another embodiment said composition to each eye of a New Zealand rabbit provides at least about 30000 ng of cyclosporin A per gram of cornea to the corneas of said rabbit.

In another embodiment said composition to each eye of a New Zealand rabbit provides at least about 45000 ng of cyclosporin A per gram of cornea to the corneas of said rabbit.

In another embodiment said composition to each eye of a New Zealand rabbit provides at least about 95000 ng of cyclosporin A per gram of cornea to the corneas of said rabbit.

In another embodiment said composition to each eye of a New Zealand rabbit provides at least about 155000 ng of cyclosporin A per gram of cornea to the corneas of said rabbit.

In another embodiment, topical administration of one 35 µL drop of said composition to each eye of a female New Zealand white rabbit provides to the conjunctivas of said rabbit at least about 6000 ng of cyclosporin A per gram of conjunctiva of said rabbit over a period of 24 hours after said topical administration.

In another embodiment, said composition is an aqueous solution containing from 0.005% to about 0.04% cyclosporin A, wherein topical administration of one 35 µL drop of said composition to each eye of a New Zealand rabbit provides at least about 6000 ng of cyclosporin A per gram of conjunctiva to the conjunctivas of said rabbit as determined by:
  topically administering said composition to each eye of each of 15 female New Zealand white rabbit test subjects; and
  determining the amount of cyclosporin A in the conjunctivas of three subjects at times of about 0.5 hours, about 2 hours, about 6 hours, about 12 hours, and about 24 after administration to said subject;
wherein the amount of cyclosporin A in the conjunctiva is determined only a single time for each subject.

In another embodiment said composition to each eye of a New Zealand rabbit provides at least about 5000 ng of cyclosporin A per gram of conjunctiva to the conjunctiva of said rabbit.

In another embodiment said composition to each eye of a New Zealand rabbit provides at least about 7000 ng of cyclosporin A per gram of conjunctiva to the conjunctiva of said rabbit.

In another embodiment said composition to each eye of a New Zealand rabbit provides at least about 10000 ng of cyclosporin A per gram of conjunctiva to the conjunctiva of said rabbit.

In another embodiment said composition to each eye of a New Zealand rabbit provides at least about 17000 ng of cyclosporin A per gram of conjunctiva to the conjunctiva of said rabbit. In another embodiment, the blood level of cyclosporin A is less than 0.1 mg/mL for a person for whom the composition has been administered twice a day topically to both eyes in 35 microliter drops for twelve months.

Pharmacokinetic Study 1

A 35 µL aliquot of one of three test formulations was topically administered to each eye of a female New Zealand White rabbit (n=3 rabbits/time point). At 0.5, 2, 6, 12, 24, 48 and 144 hours post-dose, cornea, conjunctiva, sclera, eyelid margin, nasolacrimal duct, and blood samples were collected. Samples collected from naïve rabbits (n=2) served as pre-dose samples. The quantitation ranges were 0.2-40 ng/mL in blood, 0.1-200 ng in cornea and conjunctiva, 0.1-100 ng in eyelid margin and nasolacrimal duct, and 0.1-20 ng in sclera and lacrimal gland.

The pharmacokinetic parameters of cyclosporine A in ocular tissues following a single ophthalmic instillation of one of three 0.05% cyclosporine A formulations are summarized in Table 1 below:

TABLE 1

| Tissue/Matrix | Composition F | | | Composition E | | | Compositon D | | |
| --- | --- | --- | --- | --- | --- | --- | --- | --- | --- |
| | $C_{max}$ (ng/g) | $AUC_{0-t}$ (ng · hr/g) | $t_{1/2}$ (hr) | $C_{max}$ (ng/g) | $AUC_{0-t}$ (ng · hr/g) | $t_{1/2}$ (hr) | $C_{max}$ (ng/g) | $AUC_{0-t}$ (ng · hr/g) | $t_{1/2}$ (hr) |
| Cornea | 4050 | 163000 | 41.3 | 1100 | 76200 | 41.7 | 536 | 29300 | 49.8 |
| Conjunctiva | 4460 | 18100 | 11.3 | 2560 | 11600 | 5.57 | 694 | 5290 | 4.55 |
| Sclera | 545 | 6110 | 29.7 | 136 | 2840 | 24.8 | 53.0 | 1040 | 18.7 |
| Eyelid Margin | 3120 | 38300 | 42.5 | 2020 | 42200 | 38.1 | 2450 | 27700 | 24.4 |
| Nasolacrimal Duct | 195 | 2190 | NC | 74.4 | 1190 | NC | 72.0 | 279 | NC |
| Blood | 2.21 | NC | NC | 0.441 | NC | NC | BLQ | BLQ | NC |

NC = Not calculable
BLQ = Below the limit of quantitation

Briefly summarizing, following a single ocular instillation of a 0.05% cyclosporine A formulation, the highest cyclosporine A ocular tissue exposure levels were observed from Composition F, followed by the Composition E, followed by Composition D.

Materials

Test Articles

Compositions D, E, and F, as described above, were used for these experiments.

Chemicals, Reagents and Supplies

All other chemicals were reagent grade or better.

Animals

Species, Strain, Sex, Age, Size, Source, and Identification

Female New Zealand White rabbits weighing 1.8 to 2.6 kg were purchased from Charles River (St. Constant, Quebec, Canada). A permanent ear tag was used to identify animals.

Justification

Similarities between the ocular anatomies of rabbits and humans make the rabbit an attractive animal model.

Animal Husbandry

All animals were housed in environmentally-controlled facility with a time-controlled fluorescent lighting system providing a daily 12-hour light/12-hour dark period. Room temperature was maintained between 61 and 72° F., and relative humidity between 30 and 70%. Airflow ranged from 10 to 30 air changes per hour. Temperature, humidity, and airflow were monitored by the Edstrom Watchdog system version 4.0.

The animals were provided Certified Hi-Fiber Rabbit Diet. Diet certification and analysis were provided by the vendor. No analysis outside those provided by the manufacturer was performed. Drinking water that was purified by a reverse osmosis process was offered ad libitum. Water was periodically analyzed for any contaminants that may interfere with the conduct of this study.

The manufacturer conducted analysis of animal feed.

Animal Acclimation

During the acclimatization period at Allergan, animals were kept under daily observation for any change in general health or behavior. Rabbits were quarantined for at least five days prior to the start of the study. All animals appeared healthy prior to and for the duration of the study.

Animal Termination and Disposal

Animals were euthanized via injection of at least 1 mL of sodium pentobarbital into a marginal ear vein.

Study Design and Experimental Procedures

Study Design

TABLE 1

| | Study design |
|---|---|
| Animal species and strain | Rabbit, New Zealand White |
| Gender | Female |
| Number | 3 rabbits/time point<br>2 rabbits at pre-dose (bioanalytical controls) |
| Body Weights | 1.8-2.8 kg |
| Dosing Regimen | Topical ocular, single dose, bilateral |
| Dose Volume | 35 μL |
| Test Article | Formulations containing 0.05% AGN 192371 (cyclosporine A) |
| Time Points | 0.5, 2, 6, 12, 24, 48, and 144 hours post-dose |
| Tissues/Matrices | Cornea, conjunctiva, sclera, nasolacrimal duct, eyelid margin and blood |
| Assay Method | LC-MS/MS |
| Analyte | AGN 192371 (Cyclosporine A) |
| Quantitation Range | Blood: 0.5-40 ng/mL<br>Cornea: 0.1-200 ng<br>Conjunctiva: 0.1-200 ng<br>Eyelid Margin: 0.1-100 ng<br>Nasolacrimal Duct: 0.1-100 ng<br>Sclera:: 0.1-20 ng |

Single bilateral dose, 3 rabbits (6 eyes and 3 blood samples) per time point. Two animals in group 4 were not dosed and were used as bioanalytical controls. Prior to dosing, 65 animals were weighed and assigned to 4 study groups. The study design is presented in Table 1. The four study groups are presented in the Table 2 below:

TABLE 2

| Group | Treatment | Dose (μL) | Frequency | n |
|---|---|---|---|---|
| 1 | Composition F | 35 | Single Bilateral Dose | 3F per time point (total of 21F) |
| 2 | Composition E | 35 | Single Bilateral Dose | 3F per time point (total of 21F) |
| 3 | Composition D | 35 | Single Bilateral Dose | 3F per time point (total of 21F) |
| 4 | No Dose | — | — | 2F (total of 2F) | n = Number of animals per group
F = Female

Pretreatment Examinations

Prior to placement on study, a physical examination was performed on each animal. Gross observations were recorded prior to drug administration and immediately after ocular dose using a standardized data collection sheet.

Randomization

Prior to dosing, 65 animals were weighed and randomly assigned to four study groups.

Dosing Procedure:

Animals were dosed once by ocular instillation bilaterally at Hour 0 of the study. Immediately prior to dosing, the eye was inspected for any abnormalities, such as infection, red eye, or visible damage. Only animals without visible abnormalities were used. The lower eyelid was gently pulled out and away from the eye. Using a Gilson precision pipette, 35 μL of dosing solution was instilled into the lower cul-de-sac of each eye. The time of dose administration was recorded. The eye was gently held closed for approximately 5 seconds to ensure even dose distribution around the eye. Gross ocular observations were performed following dosing. The animal, including the dosed eyes, were subjectively evaluated for signs of irritation. Observations were recorded.

Mortality/Morbidity

Animals were observed for mortality/morbidity during the study.

Body Weights

Animals were weighed the day before dose administration and subsequently randomized.

Pre-Necropsy Blood Collection

Blood was collected from each rabbit prior to euthanasia/necropsy. Animals were anesthetized with an intravenous injection of a ketamine/xylazine cocktail (87 mg/mL ketamine, 13 mg/mL xylazine) at a volume of 0.1 mL/kg. Blood was collected via cardiac puncture. Approximately 5 mL of blood was collected into 10 mL lavender top ($K_3$ EDTA) tubes. Blood samples were stored at or below approximately −15° C. until bioanalysis.

Euthanasia

Animals were euthanized with an intravenous injection of commercial euthanasia solution following blood collection.

Necropsy and Collection of Ocular Tissues

Ocular samples were collected from both eyes, blotted dry where applicable, weighed and placed in separate, appropriately labeled, silanized vials, at the time of necropsy. Both eyes were rinsed with LENS PLUS® in order to clear residual surface formulation remaining on the ocular surface.

Conjunctiva

The upper and lower conjunctiva from each eye were removed and pooled, weight recorded, placed into separate screw-cap glass 13×100 silanized test tubes and immediately placed on ice. Samples were stored at or below −15° C. until bioanalysis.

Cornea

The entire cornea was removed from each eye; weight recorded, placed into separate screw-cap glass 13×100 silanized test tubes and immediately placed on ice. Samples were stored at or below −15° C. until bioanalysis.

Sclera

The sclera was removed from each eye; weight recorded, placed into separate screw-cap glass 13×100 silanized test tubes and immediately placed on ice. Samples were stored at or below −15° C. until bioanalysis.

Nasolacrimal Duct

Tissue containing the nasolacrimal duct associated with each eye was removed; weight recorded, placed into screw-cap glass 13×100 silanized test tubes and immediately placed on ice. Samples were stored at or below −15° C. until bioanalysis.

Eyelid Margin

The eyelid margins were removed from each eye; weight recorded, placed into separate screw-cap glass 13×100 silanized test tubes and immediately placed on ice. Samples were stored at or below −15° C. until bioanalysis.

Sample Storage

Blood and ocular tissue samples were stored at or below −15° C. until bioanalysis.

Bioanalysis

Ocular tissue and blood concentrations were quantified using the following method.

Ocular tissue samples were extracted by soaking over night with 2.0 mL methanol at 4° C. This was followed by a second soak with 2.0 mL methanol and shaking for approximately one hour at room temperature. An aliquot of 1 mL from a total of 4 mL organic extract was removed (all 4 mL were analyzed for lacrimal gland samples), and internal standard added (20 μL of 500 ng/mL of CsG). The methanolic extract was evaporated to dryness and reconstituted with 200 μL of 2 mM ammonium acetate/0.4% formic acid in 50:50 acetonitrile:water for LC MS/MS analysis. The bioanalytical procedure for analysis of blood samples involved addition of internal standard, CsG (10 μL of 500 ng/mL) to 0.5 mL aliquots of K3 EDTA-treated rabbit blood.

Following incubation of blood sample for 30 minutes at 37° C., the samples were acidified with 0.1 N HCL (2 mL). Methyl t-butyl ether (4 mL) was added to each sample and mixed for 15 minutes. The organic layer was removed and made basic by addition of 0.1 N NaOH (2 mL). The organic extract was separated from the aqueous layer, evaporated to dryness and reconstituted with 200 μL of 2 mM ammonium acetate/0.4% formic acid in 50:50 acetonitrile:water for LC MS/MS analysis. Aliquots (50 μL) of the reconstituted samples were analyzed by LC-MS/MS using a PE Sciex API 3000 mass spectrometer (Applied Biosystems, Foster City, Calif.), Leap autosampler (Carrboro, N.C.), and HPLC pumps (Shimadzu Scientific Instruments, Columbia, Md.). Reverse-phase HPLC was performed on a Keystone BDS C8 column (3 μm, 2.1×50 mm, 65° C.) with solvent gradient elution (A=2 mM ammonium acetate/0.4% formic acid in water and B=2 mM ammonium acetate/0.4% formic acid in acetonitrile) at a flow rate of 0.3 mL/min. The precursor-product ion pairs used in MRM analysis were: 1203 $(MH)^+$ →425.5 for CsA and m/z 1217 $(MH)^+$→425.5 for IS(Cyclosporin G). The total analysis time was 5 min, with retention times of CsA and CsG at approximately 1.82 and 1.86 minutes, respectively.

Data Treatment

Data Collection

Pre and post treatment gross ocular examinations

Body Weights: Randomization at Day −1

Dosing Notes

Mortality/Morbidity

Blood Samples: Pre-necropsy

Ocular Tissue Samples: Post-necropsy

Data Calculation and Outlier Analysis

All data was used in calculations unless omitted for reasons justified in the raw data.

Pharmacokinetic Analysis

Thermo Electron Watson™ (Philadelphia, Pa.) and Microsoft® Excel (Redmond, Wash.) were used for pharmacokinetic calculations. The pharmacokinetic parameters listed below were calculated using a known non-compartmental approach (see Tang-Lui, et. al. *Pharmaceutical Research*, Vol 5, No. 4, 1988, 238-241). The pharmacokinetic data was described using descriptive statistics such as mean and standard deviation whenever possible. Area under the concentration-time profile (AUC) values were reported as a composite AUC and whenever possible, ±standard error of the mean (SEM).

| PK Parameter | Description |
| --- | --- |
| $C_{max}$ (ng/mL) or (ng/g) | Maximum observed concentration |
| $T_{max}$ (hr) | Time corresponding to maximum observed concentration |
| $AUC_{0-t}$ (ng · hr/g) | Area under concentration time curve from time zero to the last quantifiable time point using the random method for non-sequential sampling |
| $t_{1/2}$ (hr) | Half-life |
| MRT (hr) | Mean residence time |

Values Below the Limit of Quantitation and Number Rounding

If more than half of the concentration values contributing to a calculation of the mean were below limit of quantitation (BLQ), then the statistics were reported as non-calculable (NC). If half or more of the values were quantifiable, then any BLQ values were replaced with a value of "0", and the mean and its standard deviation (SD) were calculated with these replaced values. The mean and standard deviation of the mean were calculated at each sampling time point within each treatment group. Whenever the sample size was less than or equal to 2, only mean values were listed. All mean values were reported to 3 significant figures and standard deviations were reported to the same decimal place as their respective mean values.

Protocol Deviations

Prior to collection of ocular tissue samples at the 6 hour time point, the eyes were not rinsed with Lens Plus® to clear any residual surface formulation remaining on the ocular surface. It is believed that this deviation will have minimal impact on the results derived from this study since in general this drug is rapidly absorbed from the ocular surface. In addition, blinking by the rabbits over 6 hours should also act to clear any residual surface formulation.

Abbreviations

| | |
|---|---|
| ACN | Acetonitrile |
| ALQ | Above Limits of Quantitation |
| AUC | Area Under the Plasma or Blood Drug Concentration - Time Curve |
| $AUC_{Extrap}$ | Extrapolated Area Under the Plasma or Blood Drug Concentration Time Curve from Time 0 to the Last Quantifiable Timepoint |
| BID | Two Times Daily |
| BLQ | Below Limit of Quantitation |
| BMS | Bioanalytical Mass Spectrometry |
| CFR | Code of Federal Regulations |
| C0 or $C_0$ | Extrapolated Plasma or Blood Drug Concentrations at the Time 0 |
| Cmax or $C_{max}$ | Maximal Drug Concentration |
| CONC | Concentration |
| DG | Day of Gestation |
| DSE | Drug Safety Evaluation |
| $EDTA(K_3)$ | Potassium Ethylenediaminetetraacetic Acid |
| F | Female |
| GD | Gestation Day |
| FDA | United States Food and Drug Administration |
| GLP | Good Laboratory Practice |
| IC | Intracardiac |
| IS | Insufficient Sample Received |
| IM | Intramuscular |
| IU | International Units |
| IV | Intravenous |
| IVT | Intravitreal |
| LC-MS/MS | Liquid Chromatography Tandem Mass Spectrometry |
| LLOQ | Lower Limit of Quantitation |
| M | Male |
| N, n, No., no. | Number |
| N/A, N.A., or n/a | Not Applicable |
| N/C, N.C., NC, or n/c | Not Calculable |
| NR | No Result/Not Reported |
| NS | No Sample |
| NZW | New Zealand White |
| OD | Right Eye |
| OU | Both Eyes |
| PKDM | Pharmacokinetics and Drug Metabolism |
| PO | By Mouth |
| QID | Four Times Daily |
| QNS | Quantity Not Sufficient |
| SD, S.D., or sd | Standard Deviation |
| SE | Standard Error |
| Sec | Seconds |
| SMP | Sample |
| T½ or $T_{1/2}$ | Drug Half Life |
| TA | Triamcinolone Acetonide |
| TID | Three Times Daily |
| TK | Toxicokinetic |
| Tmax or $T_{max}$ | Time at which $C_{max}$ is Observed |
| U | Units |
| ULOQ | Upper Limit of Quantitation |

Note:
Not all abbreviations listed may appear in this report.

Results and Discussion

Cornea

The mean concentrations and pharmacokinetic parameters are summarized in Tables 3 and 4. The concentration-time profiles of cyclosporine A in cornea following a single bilateral ocular administration of one of three 0.05% cyclosporine A formulations to rabbits are presented in FIG. 1.

TABLE 3

Mean cornea concentrations of cyclosporine A following a single bilateral topical ocular instillation of one of three 0.05% cyclosporine A formulations to New Zealand White rabbits.

| | Cyclosporine A concentration (ng/g) | | | | | |
|---|---|---|---|---|---|---|
| Time | Composition F | | Composition E | | Composition D | |
| (hr) | Mean | SD | Mean | SD | Mean | SD |
| 0.5 | 4050 | 1220 | 1020 | 330 | 295 | 201 |
| 2 | 2740 | 620 | 1100 | 190 | 432 | 142 |
| 6 | 3030 | 750 | 1010 | 170 | 536 | 138 |
| 12 | 2530 | 430 | 858 | 267 | 417 | 127 |
| 24 | 1570$^a$ | 390 | 891$^a$ | 115 | 256$^a$ | 28.2 |
| 48 | 1240$^a$ | 230 | 622$^a$ | 118 | 238$^a$ | 76.6 |
| 144 | 222$^a$ | 61 | 125$^a$ | 47 | 52.5$^a$ | 13.2 |

Mean values represent an average of n = 6
$^a$Concentration time points used to calculate $t_{1/2}$

TABLE 4

Pharmacokinetic parameters in cornea of cyclosporine A following a single bilateral topical ocular instillation of one of three 0.05% cyclosporine A formulations to New Zealand White rabbits.

| Parameter | Composition F | Composition E | Composition D |
|---|---|---|---|
| $C_{max}$ (ng/g) | 4050 ± 1220 | 1100 ± 190 | 536 ± 138 |
| $T_{max}$ (hr) | 0.500 | 2.00 | 6.00 |
| $AUC_{0-t}$ (ng · hr/g)$^a$ | 163000 ± 7000 | 76200 ± 3300 | 29300 ± 2000 |
| $AUC_{0-24}$ (ng · hr/g) | 59000 | 22100 | 9450 |
| $t_{1/2}$ (hr) | 41.3 | 42.2 | 49.8 |
| MRT (hr) | 50.3 | 56.5 | 61.6 |

$^a$An AUC interval of 0-144 hours was used for calculations for the three formulations Composition F Following a single bilateral ocular instillation of Composition F, cyclosporine A was rapidly absorbed into the cornea with a peak corneal concentration ($C_{max}$) of 4050±1220 ng/g, occurring 0.500 hours post-dose. The area under the concentration-time curve ($AUC_{0-t}$) value through the last quantifiable time point was 163000±7000 ng·hr/g and the $AUC_{0-24}$ value was 59000 ng·hr/g. The terminal half-life ($t_{1/2}$) was 41.3 hours and the mean residence time (MRT) was 50.3 hours.

Composition E

Following a single bilateral ocular instillation of Composition E, cyclosporine A was absorbed into the cornea with $C_{max}$ value of 1100±190 ng/g, occurring 2.00 hours post-dose. The $AUC_{0-t}$ value was 76200±3300 ng·hr/g and the $AUC_{0-24}$ value was 22100 ng·hr/g. The terminal $t_{1/2}$ was 41.7 hours and the MRT was 56.5 hours.

Composition D

Following a single bilateral ocular instillation of Composition D, cyclosporine A was absorbed into the cornea with a $C_{max}$ value of 536±138 ng/g, occurring 6.00 hours post-dose. The $AUC_{0-t}$ value was 29300±2000 ng·hr/g and the $AUC_{0-24}$ value was 9450 ng·hr/g. The terminal $t_{1/2}$ was 49.8 hours and the MRT was 61.6 hours.

Conjunctiva

Figure 2:
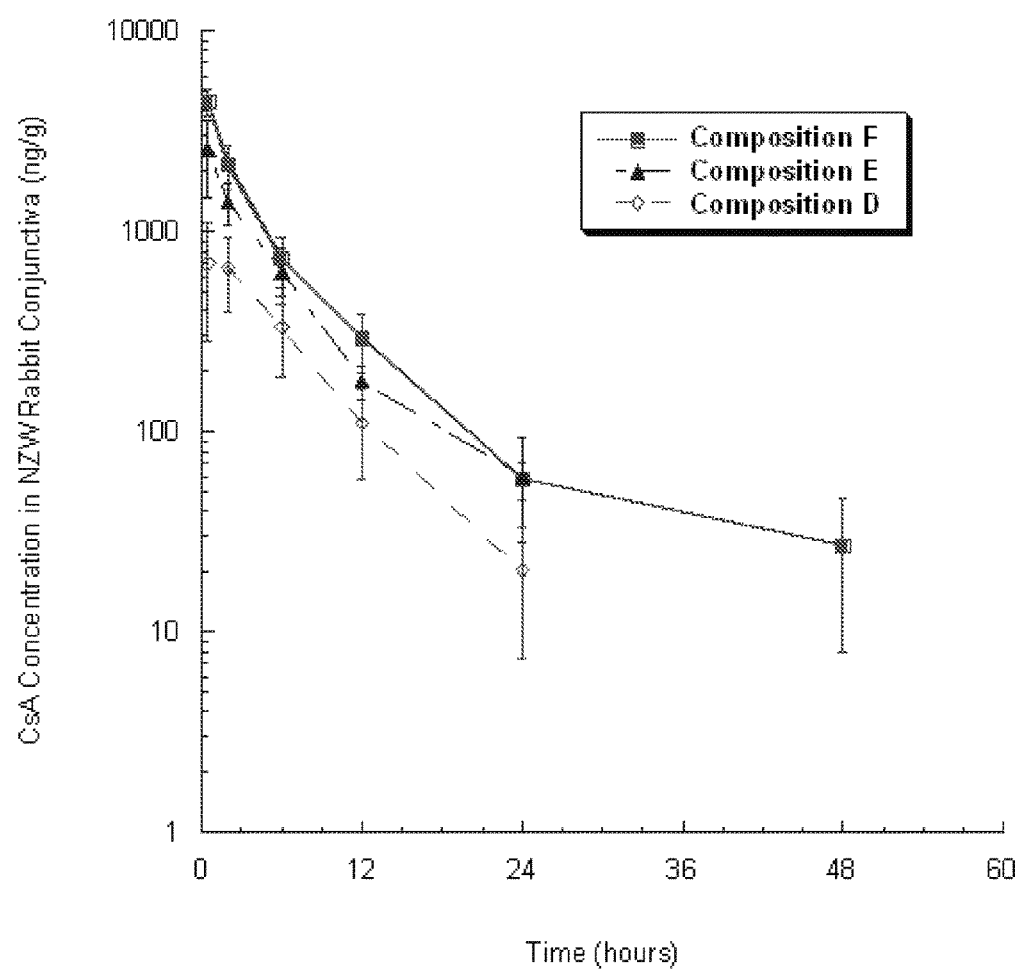
FIG. 2 Mean (±SD) conjunctiva cyclosporine A concentrations (semi-log) following a single bilateral topical ocular instillation of one of three 0.05% cyclosporine A formulations to New Zealand White rabbits.

The mean concentrations and pharmacokinetic parameters are summarized in Tables 5 and 6. The concentration-time profiles of cyclosporine A in conjunctiva following a single bilateral ocular administration of one of three 0.05% cyclosporine A formulations to rabbits are presented in FIG. 2.

TABLE 5

Mean conjunctiva concentrations of cyclosporine A following a single bilateral topical ocular instillation of one of three 0.05% cyclosporine A formulations to New Zealand White rabbits.

| Time | Cyclosporine A concentration (ng/g) | | | | | |
|---|---|---|---|---|---|---|
| | Composition F | | Composition E | | Composition D | |
| (hr) | Mean | SD | Mean | SD | Mean | SD |
| 0.5 | 4460 | 650 | 2560 | 1070 | 694 | 410 |
| 2 | 2170 | 530 | 1410 | 330 | 665 | 266 |
| 6 | 739 | 208 | 630$^a$ | 197 | 330$^a$ | 143 |
| 12 | 292$^a$ | 97 | 178$^a$ | 34 | 110$^a$ | 52.3 |
| 24 | 58.2$^a$ | 12.5 | 60.5$^a$ | 32.5 | 20.5$^a$ | 13.2 |
| 48 | 26.9$^a$ | 19.1 | BLQ | — | BLQ | — |
| 144 | BLQ | — | BLQ | — | BLQ | — |

Mean values represent an average of n = 6
BLQ = Below the limit of quantitation
$^a$Concentration time points used to calculate $t_{1/2}$

TABLE 6

Pharmacokinetic parameters in conjunctiva of cyclosporine A following a single bilateral topical ocular instillation of one of three 0.05% cyclosporine A formulations to New Zealand White rabbits.

| Parameter | Composition F | Composition E | Composition D |
|---|---|---|---|
| $C_{max}$ (ng/g) | 4460 ± 650 | 2560 ± 1070 | 694 ± 410 |
| $T_{max}$ (hr) | 0.500 | 0.500 | 0.500 |
| $AUC_{0-t}$ (ng · hr/g) | 18100 ± 800$^a$ | 11600 ± 700$^b$ | 5290 ± 480$^b$ |
| $AUC_{0-24}$ (ng · hr/g) | 17100 | 11600 | 5290 |
| $t_{1/2}$ (hr) | 11.3 | 5.57 | 4.55 |
| MRT (hr) | 7.37 | 5.93 | 6.07 |

$^a$An AUC interval of 0-48 hours was used for calculations
$^b$An AUC interval of 0-24 hours was used for calculations Composition F Following a single bilateral ocular instillation of Composition F, cyclosporine A was rapidly absorbed into the conjunctiva with a $C_{max}$ value of 4460±650 ng/g, occurring 0.500 hours post-dose. The $AUC_{0-t}$ value was 18100±800 ng·hr/g and the $AUC_{0-24}$ value was 17100 ng·hr/g. The terminal $t_{1/2}$ was 11.3 hours and the MRT was 7.37 hours.

Composition E

Following a single bilateral ocular instillation of Composition E, cyclosporine A was rapidly absorbed into the conjunctiva with a $C_{max}$ value of 2560±1070 ng/g, occurring 0.500 hours post-dose. The $AUC_{0-t}$ value was 11600±700 ng·hr/g. The terminal $t_{1/2}$ was 5.57 hours and the MRT was 5.93 hours.

Composition D

Following a single bilateral ocular instillation of Composition D, cyclosporine A was rapidly absorbed into the conjunctiva with a $C_{max}$ value of 694±410 ng/g, occurring 0.500 hours post-dose. The $AUC_{0-t}$ value was 5290±480 ng·hr/g. The terminal $t_{1/2}$ was 4.55 hours and the MRT was 6.07 hours.

Sclera

Figure 3:
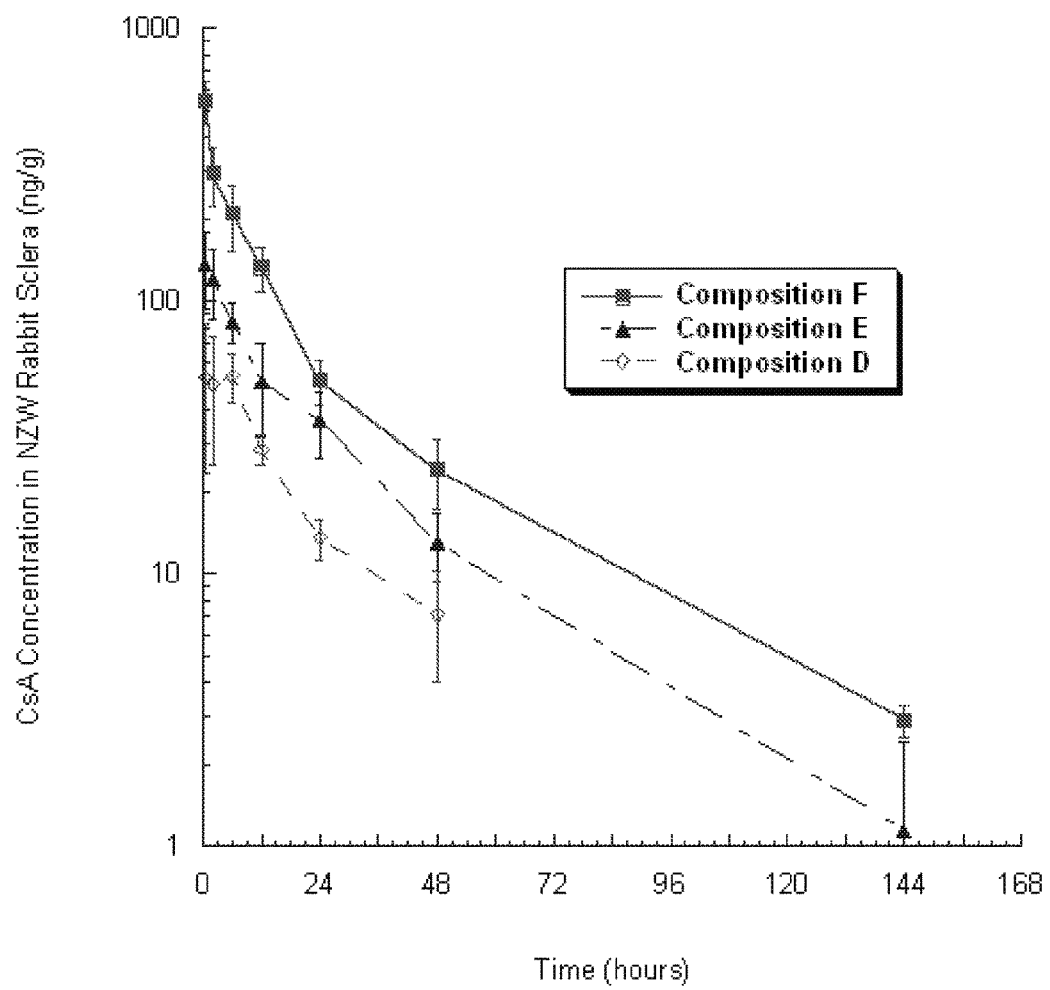
FIG. 3 Mean (±SD) sclera cyclosporine A concentrations (semi-log) following a single bilateral topical ocular instillation of one of three 0.05% cyclosporine A formulations to New Zealand White rabbits.

The mean concentrations and pharmacokinetic parameters are summarized in Tables 7 and 8. The concentration-time profiles of cyclosporine A in sclera following a single bilateral ocular administration of one of three 0.05% cyclosporine A formulations to rabbits are presented in FIG. 3.

TABLE 7

Mean sclera concentrations of cyclosporine A following a single bilateral topical ocular instillation of one of three 0.05% cyclosporine A formulations to New Zealand White rabbits.

| Time | Cyclosporine A concentration (ng/g) | | | | | |
|---|---|---|---|---|---|---|
| | Composition F | | Composition E | | Composition D | |
| (hr) | Mean | SD | Mean | SD | Mean | SD |
| 0.5 | 545 | 98 | 136 | 44 | 52.5 | 29.3 |
| 2 | 294 | 74 | 120 | 34 | 49.4 | 24.5 |
| 6 | 210 | 58 | 83.7 | 14.0 | 53.0 | 10.9 |
| 12 | 133 | 25 | 51.0 | 19.1 | 28.6$^a$ | 3.7 |
| 24 | 51.4$^a$ | 9.4 | 36.5$^a$ | 9.9 | 13.5$^a$ | 2.3 |
| 48 | 24.2$^a$ | 7.1 | 13.0$^a$ | 3.61 | 7.10$^a$ | 3.09 |
| 144 | 2.92$^a$ | 0.40 | 1.14$^a$ | 1.27 | BLQ | — |

Mean values represent an average of n = 6
BLQ = Below the limit of quantitation
$^a$Concentration time points used to calculate $t_{1/2}$

TABLE 8

Pharmacokinetic parameters in sclera of cyclosporine A following a single bilateral topical ocular instillation of one of three 0.05% cyclosporine A formulations to New Zealand White rabbits.

| Parameter | Composition F | Composition E | Composition D |
|---|---|---|---|
| $C_{max}$ (ng/g) | 545 ± 98 | 136 ± 43 | 53.0 ± 10.9 |
| $T_{max}$ (hr) | 0.500 | 0.500 | 6.00 |
| $AUC_{0-t}$ (ng · hr/g) | 6110 ± 260$^a$ | 2840 ± 150$^a$ | 1040 ± 50$^b$ |
| $AUC_{0-24}$ (ng · hr/g) | 3900 | 1560 | 792 |
| $t_{1/2}$ (hr) | 29.7 | 24.8 | 18.7 |
| MRT (hr) | 25.3 | 26.9 | 23.8 |

$^a$An AUC interval of 0-144 hours was used for calculations
$^b$An AUC interval of 0-48 hours was used for calculations Following a single bilateral ocular instillation of Composition F, cyclosporine A was rapidly absorbed into the sclera with a $C_{max}$ value of 545±98 ng/g, occurring 0.500 hours post-dose. The $AUC_{0-t}$ value was 6110±260 ng·hr/g and the $AUC_{0-24}$ value was 3900 ng·hr/g. The terminal $t_{1/2}$ was 29.7 hours and the MRT was 25.3 hours.

Composition E

Following a single bilateral ocular instillation of Composition E, cyclosporine A was rapidly absorbed into the sclera with a $C_{max}$ value of 136±43 ng/g, occurring 0.500 hours post-dose. The $AUC_{0-t}$ value was 2840±150 ng·hr/g and the $AUC_{0-24}$ value was 1560 ng·hr/g. The terminal $t_{1/2}$ was 24.8 hours and the MRT was 26.7 hours.

Composition D

Following a single bilateral ocular instillation of Composition D, cyclosporine A was absorbed into the sclera with a $C_{max}$ value of 53.0±10.9 ng/g, occurring 6.00 hours post-dose. The $AUC_{0-t}$ value was 1040±50 ng·hr/g and the $AUC_{0-24}$ value was 792 ng·hr/g. The terminal $t_{1/2}$ was 18.7 hours and the MRT was 23.8 hours.

Eyelid Margin

Figure 4:
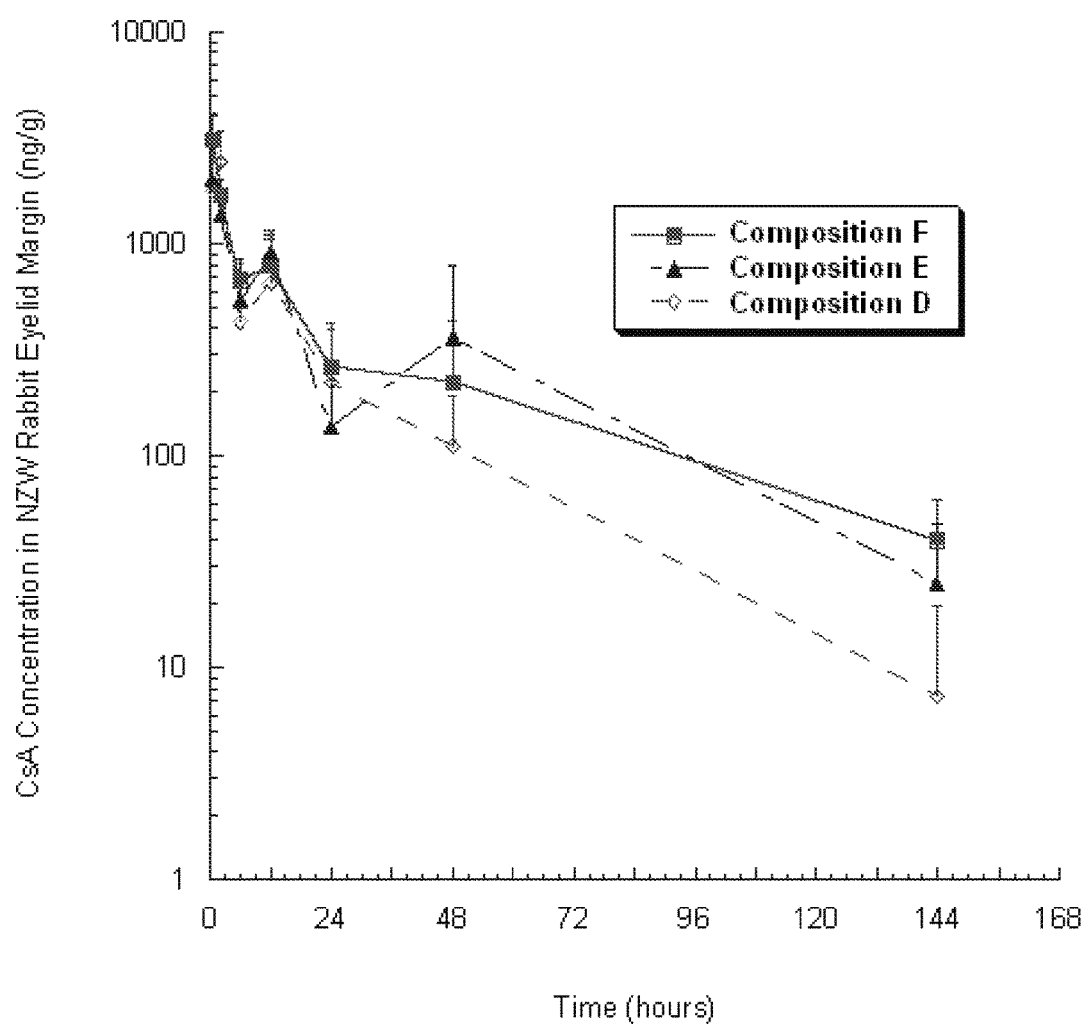
FIG. 4 Mean (±SD) eyelid margin cyclosporine A (concentrations (semi-log) following a single bilateral topical ocular instillation of one of three 0.05% cyclosporine A formulations to New Zealand White rabbits.

The mean concentrations and pharmacokinetic parameters are summarized in Tables 9 and 10. The concentration-time profiles of cyclosporine A in the eyelid margin following a single bilateral ocular administration of one of three 0.05% cyclosporine A formulations to rabbits are presented in FIG. 4.

TABLE 9

Mean eyelid margin concentrations of cyclosporine A following a single bilateral topical ocular instillation of one of three 0.05% cyclosporine A formulations to New Zealand White rabbits.

| | Cyclosporine A concentration (ng/g) | | | | | |
|---|---|---|---|---|---|---|
| | Composition F | | Composition E | | Composition D | |
| Time (hr) | Mean | SD | Mean | SD | Mean | SD |
| 0.5 | 3120 | 1040 | 2020 | 980 | 1800 | 900 |
| 2 | 1710 | 300 | 1380 | 630 | 2450 | 970 |
| 6 | 679 | 135 | 547 | 300 | 430 | 214 |
| 12 | 787 | 280 | 910 | 199 | 662 | 506 |
| 24 | 263[a] | 158 | 138[a] | 87 | 222[a] | 172 |
| 48 | 223[a] | 207 | 362[a] | 437 | 112[a] | 82 |
| 144 | 40.0[a] | 22.5 | 24.9[a] | 23.4 | 7.30[a] | 12.64 |

Mean values represent an average of n = 6
[a]Concentration time points used to calculate $t_{1/2}$

TABLE 10

Pharmacokinetic parameters in eyelid margin of cyclosporine A following a single bilateral topical ocular instillation of one of three 0.05% cyclosporine A formulations to New Zealand White rabbits.

| Parameter | Composition F | Composition E | Composition D |
|---|---|---|---|
| $C_{max}$ (ng/g) | 3120 ± 1040 | 2020 ± 980 | 2450 ± 970 |
| $T_{max}$ (hr) | 0.500 | 0.500 | 2.00 |
| $AUC_{0-t}$ (ng · hr/g)[a] | 38300 ± 5300 | 42200 ± 10800 | 27700 ± 3300 |
| $AUC_{0-24}$ (ng · hr/g) | 19900 | 17600 | 18000 |
| $t_{1/2}$ (hr) | 42.5 | 38.2 | 24.4 |
| MRT (hr) | 40.5 | 38.4 | 21.9 |

[a]An AUC interval of 0-144 hours was used for calculations for the three formulations Composition F Following a single bilateral ocular instillation of Composition F, cyclosporine A was rapidly absorbed into the eyelid margin with a $C_{max}$ value of 3120±1040 ng/g, occurring 0.500 hours post-dose. The $AUC_{0-t}$ value was 38300±5300 ng·hr/g and the $AUC_{0-24}$ value was 19900 ng·hr/g. The terminal $t_{1/2}$ was 42.5 hours and the MRT was 40.5 hours.

Composition E

Following a single bilateral ocular instillation of Composition E, cyclosporine A was rapidly absorbed into the eyelid margin with a $C_{max}$ value of 2020±980 ng/g, occurring 0.500 hours post-dose. The $AUC_{0-t}$ value was 42200±10800 ng·hr/g and the $AUC_{0-24}$ value was 17600 ng·hr/g. The terminal $t_{1/2}$ was 38.1 hours and the MRT was 38.4 hours.

Composition D

Following a single bilateral ocular instillation of Composition D, cyclosporine A was absorbed into the eyelid margin with a $C_{max}$ value of 2450±970 ng/g, occurring 2.00 hours post-dose. The $AUC_{0-t}$ value was 27700±3300 ng·hr/g and the $AUC_{0-24}$ value was 18000 ng·hr/g. The terminal $t_{1/2}$ was 24.4 hours and the MRT was 21.9 hours.

Nasolacrimal Duct

Figure 5:
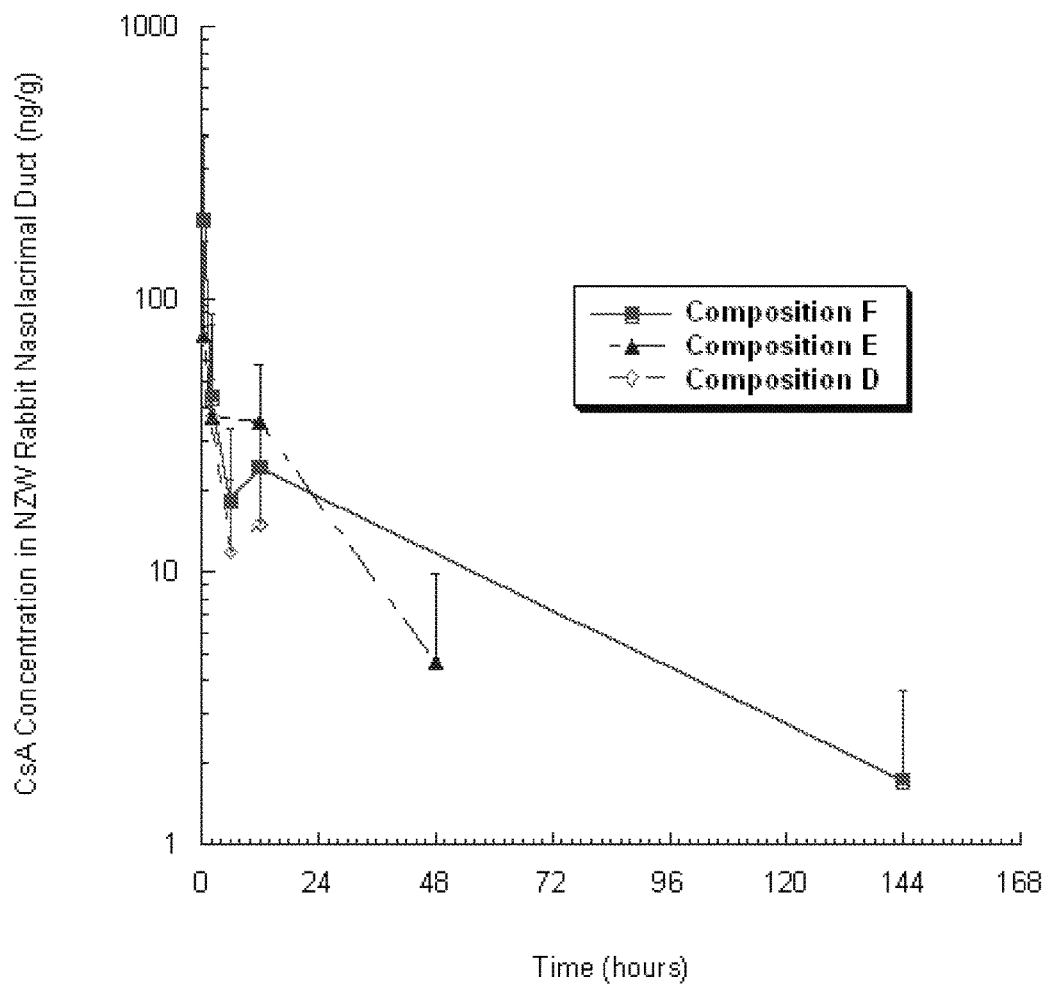
FIG. 5 Mean (±SD) nasolacrimal duct cyclosporine A concentrations (semi-log) following a single bilateral topical ocular instillation of one of three 0.05% cyclosporine A formulations to New Zealand White rabbits.

The mean concentrations and pharmacokinetic parameters are summarized in Tables 11 and 12. The concentration-time profiles of cyclosporine A in nasolacrimal duct tissue following a single bilateral ocular administration of one of three 0.05% cyclosporine A formulations to rabbits are presented in FIG. 5.

TABLE 11

Mean nasolacrimal duct concentrations of cyclosporine A following a single bilateral topical ocular instillation of one of three 0.05% cyclosporine A formulations to New Zealand White rabbits.

| | Cyclosporine A concentration (ng/g) | | | | | |
|---|---|---|---|---|---|---|
| | Composition F | | Composition E | | Composition D | |
| Time (hr) | Mean | SD | Mean | SD | Mean | SD |
| 0.5 | 194 | 201 | 74.4 | 20.9 | 72.0 | 91.7 |
| 2 | 43.7 | 44.1 | 37.2 | 43.6 | 37.4 | 13.8 |
| 6 | 18.2 | 15.2 | BLQ | — | 11.8 | 10.0 |
| 12 | 24.2 | 12.0 | 35.5 | 21.5 | 14.9 | 8.4 |
| 24 | BLQ | — | BLQ | — | BLQ | — |
| 48 | BLQ | — | 4.68 | 5.15 | BLQ | — |
| 144 | 1.71 | 1.93 | BLQ | — | BLQ | — |

Mean values represent an average of n = 6
BLQ = Below the limit of quantitation

TABLE 12

Pharmacokinetic parameters in nasolacrimal duct of Cyclosporine A following a single bilateral topical ocular instillation of one of three 0.05% cyclosporine A formulations to New Zealand White rabbits.

| Parameter | Composition F | Composition E | Composition D |
|---|---|---|---|
| $C_{max}$ (ng/g) | 195 ± 201 | 74.4 ± 20.9 | 72.0 ± 91.7 |
| $T_{max}$ (hr) | 0.500 | 0.500 | 0.500 |
| $AUC_{0-t}$ (ng · hr/g) | 2190 ± 350[a] | 1190 ± 212[b] | 279 ± 39[c] |
| $AUC_{0-12}$ (ng · hr/g) | 478 ± 86 | 465 ± 106 | 279 ± 39 |
| $t_{1/2}$ (hr) | NC | NC | NC |
| MRT (hr)[d] | 17.6 | 24.7 | 12.1 |

NC = Not calculable
[a]An AUC interval of 0-144 hours was used for calculations
[b]An AUC interval of 0-48 hours was used for calculations
[c]An AUC interval of 0-12 hours was used for calculations
[d]A time interval of 0-12 hours was used for calculations Composition F Following a single bilateral ocular instillation of Composition F, cyclosporine A rapidly drained into and was then absorbed into the nasolacrimal duct tissue with a $C_{max}$ value of 195±201 ng/g, occurring 0.500 hours post-dose. The $AUC_{0-t}$ value was 2190±350 ng·hr/g and the $AUC_{0-12}$ value was 478±86 ng·hr/g. The MRT was 17.6 hours.

Composition E

Following a single bilateral ocular instillation of Composition E, cyclosporine A rapidly drained into and was then absorbed into the nasolacrimal duct tissue with a $C_{max}$ value of 74.4±20.9 ng/g, occurring 0.500 hours post-dose. The $AUC_{0-t}$ value was 1190±210 ng·hr/g and the $AUC_{0-12}$ value was 465±106 ng·hr/g. The MRT was 24.7 hours.

Composition D

Following a single bilateral ocular instillation of Composition D, cyclosporine A rapidly drained into and was then absorbed into the nasolacrimal duct tissue with a $C_{max}$ value of 72.0±91.7 ng/g, occurring 0.500 hours post-dose. The $AUC_{0-t}$ value was 279±39 ng·hr/g. The MRT was 12.1 hours.

Blood

The mean concentrations of cyclosporine A in blood are summarized in Table 13.

TABLE 13

Mean blood concentrations of Cyclosporine A following a single bilateral topical ocular instillation of one of three 0.05% cyclosporine A formulations to New Zealand White rabbits.

| Time | Cyclosporine A concentration (ng/mL) | | | | | |
|---|---|---|---|---|---|---|
| | Composition F | | Composition E | | Composition D | |
| (hr) | Mean | SD | Mean | SD | Mean | SD |
| 0.5 | 2.21 | 0.33 | 0.441 | 0.126 | BLQ | — |
| 2 | 0.463 | 0.021 | BLQ | — | BLQ | — |
| 6 | BLQ | — | BLQ | — | BLQ | — |
| 12 | BLQ | — | BLQ | — | BLQ | — |
| 24 | BLQ | — | BLQ | — | BLQ | — |
| 48 | BLQ | — | BLQ | — | BLQ | — |
| 144 | BLQ | — | BLQ | — | BLQ | — |

Mean values represent an average of n = 3
BLQ = Below the limit of quantitation

Composition F

Following a single bilateral ocular instillation of Composition F, cyclosporine A was detected at 0.5 and 2 hours post-dose in the blood at concentrations of 2.21±0.33 ng/mL and 0.463±0.021 ng/mL, respectively. Cyclosporine A levels were below the limit of quantitation at all subsequent time points.

Composition E

Following a single bilateral ocular instillation of Composition E, cyclosporine A was detected at 0.5 hours post-dose in the blood at a concentration of 0.441±0.126 ng/mL. Cyclosporine A levels were below the limit of quantitation at all subsequent time points.

Composition D

Following a single bilateral ocular instillation of Composition D, cyclosporine A levels were below the limit of quantitation at all time points.

Administration of Composition F to rabbits generally delivered the highest levels of cyclosporine A to ocular tissues, on average a 5-fold increase in area under the concentration-time profile (AUC) was observed when compared to Composition D. Administration of Composition E to rabbits resulted on average in a 2-fold increase in AUC when compared to Composition D. The pharmacokinetic profile observed following Composition D administration to New Zealand White rabbits in this study was in good agreement with previously reported data.

In general, the terminal half-life and mean residence time observed were greatest for Composition F, followed by the Composition E, followed by Composition D. Thus, AUC values were reported to the last quantifiable time point, in addition to AUC through 24 hours for cornea, conjunctiva, sclera and eyelid margin and AUC through 12 hours for nasolacrimal duct to make an assessment over the same interval as to the drug levels achieved following once a day dosing. Overall, the trends observed when comparing $AUC_{0-t}$ values were consistent with the trends observed when comparing $AUC_{0-24}$ or $AUC_{0-12}$.

In conclusion, following a single ocular instillation of a 0.05% cyclosporine A formulation, the highest cyclosporine A ocular tissue exposure levels were observed when drug was formulated as an aqueous Composition F, followed by the Composition E followed by Composition D. A concomitant trend was observed in blood drug exposure.

While not intending to limit the scope of the invention, it is believed that these pharmacokinetic results suggest that significantly lower concentrations of cyclosporin A may be used in topical ophthalmic compositions than previously known and still achieve a therapeutically effective amount cyclosporin A.

Pharmacokinetic Study 2

The compositions below were prepared in an analogous manner to compositions D, E, and F.

| | Formulations | | |
|---|---|---|---|
| Ingredients | Composition G Aqueous Solution | Composition H Aqueous Solution | Composition D Emulsion |
| Cyclosporine A | 0.020 | 0.030 | 0.050 |
| Purite | 0.01% (100 ppm) | 0.01% (100 ppm) | 0.0% (0 ppm) |
| Polysorbate 80 | 1.0 | 1.0 | 1.0 |
| Glycerin | 1.0 | 1.0 | 2.2 |
| Mannitol | 0.5 | 0.5 | N/A |
| Sodium Carboxymethylcellulose (CMC) - 7LFPH | 0.5 | 0.5 | N/A |
| Sodium Citrate Dihydrate | 0.4 | 0.4 | N/A |
| Boric Acid | 0.25 | 0.25 | N/A |
| Sodium Borate Decahydrate | 0.41 | 0.41 | N/A |
| Potassium Chloride | 0.14 | 0.14 | N/A |
| Castor Oil | N/A | N/A | 1.25 |
| Pemulen TR-2 | N/A | N/A | 0.05 |
| Sodium Hydroxide | N/A | N/A | pH 7.4 |
| Purified Water | QS | QS | N/A |

A pharmacokinetic study was carried out using similar analytical methods to those already described. The parameters are shown below.

| | |
|---|---|
| Test Formulations: | G, H, and D |
| Animal species/strain: | Rabbit NZW |
| Gender: | Female |
| Number: | 2 rabbits/timepoint (2 rabbits blanks) |
| Dosing Route: | Topical ocular |
| Dosing Regimen: | Bilateral, QD(Aqueous)/BID (Composition D) - 5 days |
| Dose Volume: | 35 µL |
| Time points: | Day 1 and Day 5 - 0.5, 2, 6, 12, 24 hr post dose |
| Assay Method: | LC-MS/MS |
| Analyte: | Cyclosporine A |
| Data Analysis: | $C_{max}$, $AUC_{0-24}$, AUC dose normalized |

The results in cornea, tear, and blood are shown in the tables below.

TABLE 14

Cyclosporin bioavailability in the cornea.

| | Composition G | | Composition H | | Composition D Emulsion, BID | |
|---|---|---|---|---|---|---|
| | Day 1 | Day 5 | Day 1 | Day 5 | Day 1 | Day 5 |
| $C_{max}$ (ng/g) | 810 ± 530 | 2570 ± 650 | 1420 ± 930 | 3020 ± 440 | 583 ± 209 | 1670 ± 170 |
| $AUC_{0-24}$ (ng · hr/g) | 14700 ± 2500 | 33900 ± 2200 | 22100 ± 2800 | 48800 ± 3900 | 12100 ± 700 | 27900 ± 1000 |
| AUC/Dose (ng · hr/g/ng) | 2.12 | 4.93 | 2.12 | 4.71 | 0.349 | 0.807 |
| Total Dose/24 hr (ng) | 7000 | 7000 | 10500 | 10500 | 35000 | 35000 |

TABLE 15

Cyclosporin bioavailability in the blood.

| | 0.02% CsA Aqueous, QD | | 0.03% CsA Aqueous, QD | | Restasis ® (0.05%) Emulsion, BID | |
|---|---|---|---|---|---|---|
| | Day 1 | Day 5 | Day 1 | Day 5 | Day 1 | Day 5 |
| $C_{0.5\ hr}$ (ng/mL) | 0.741 | 0.883 | 0.727 | 0.604 | BLQ | BLQ | n = 2 rabbits/timepoint
BLQ—Below the limit of detection (0.2 ng/mL)

TABLE 16

Cyclosporin bioavailability in the tears.

| | 0.02% CsA Aqueous, QD | | 0.03% CsA Aqueous, QD | | Restasis ® (0.05%) Emulsion, BID | |
|---|---|---|---|---|---|---|
| | Day 1 | Day 5 | Day 1 | Day 5 | Day 1 | Day 5 |
| $C_{max}$ (ng/mL) | 18.2 ± 6.3 | 50.1 ± 29.2 | 31.4 ± 45.2 | 39.4 ± 9.7 | 44.2 ± 18.4 | 83.5 ± 33.2 |
| $AUC_{0-24}$ (ng · hr/mL) | 109 ± 15 | 371 ± 62 | 327 ± 121 | 397 ± 127 | 368 ± 51 | 663 ± 110 |

Standard Compositions

These compositions (AA-MM) are particularly contemplated for use as standards for comparison for characterization of the compositions disclosed herein.

The following compositions are intended to mean those identical to those disclosed in Kanai et. al., *Transplantation Proceedings*, Vol 21, No 1 (February), 1989: 3150-3152, which is incorporated by reference herein:

Composition AA: a solution consisting of 0.025% cyclosporin A, 40 mg/mL alpha cyclodextrin, and water;

Composition BB: a solution consisting of 0.009% cyclosporin A, 20 mg/mL alpha cyclodextrin, and water; and Composition CC: a solution consisting of 0.003% cyclosporin A, 10 mg/mL alpha cyclodextrin, and water.

The following composition is intended to mean those identical to that disclosed in Cheeks et. al., *Current Eye Research*, Vol 11, No 7 (1992), 641-649, which is incorporated by reference herein:

Composition DD: an alpha cyclodextrin solution at 40 mg/mL containing 0.025% cyclosporin A.

The following composition is intended to mean that identical that disclosed in Tamilvanan, Stp Pharma Sci November-December; 11(6):421-426, which is incorporated by reference herein, except that the concentration of cyclosporin A is different.

Composition EE: an emulsion consisting of cyclosporin A (0.05 w/w %), castor oil (2.5 w/w %), stearylamine (0.12 w/w %), α-tocopherol (0.01 w/w %), benzalkonium chloride (0.01 w/w %) and water up to 100 w/w %.

The following compositions are intended to mean those identical to Samples C-E disclosed in U.S. Pat. No. 5,051,402 (column 7). The entire disclosure is incorporated herein by reference.

Composition FF: 0.25 mL/mL of cyclosporin A, 40 mg/mL of α-cyclodextrin, and 7.79 mg/mL of sodium chloride;

Composition GG: 0.10 mL/mL of cyclosporin A, 20 mg/mL of α-cyclodextrin, and 8.40 mg/mL of sodium chloride; and Composition HH: 0.05 mL/mL of cyclosporin A, 10 mg/mL of α-cyclodextrin, and 8.70 mg/mL of sodium chloride.

The following composition is intended to mean that identical that disclosed in Abdulrizak, Stp Pharma Sci November-December; 11(6):427-432, which is incorporated by reference herein, except that the concentration of cyclosporin A is different.

Composition II: an emulsion consisting of cyclosporin A (0.05 w/w %), castor oil (2.5 w/w %), Poloxamer 188, (0.425 w/w %), glycerol (2.25 w/w %), Lipoid E-80

(0.5 w/w %), stearylamine (0.12 w/w %), tocopherol (0.01 w/w %), benzalkonium chloride (0.01 w/w %), and water.

The following composition is intended to mean that identical to that disclosed in Kuwano Mitsuaki et al. Pharm Res 2002 August; 19(1):108-111.

Composition JJ: a solution consisting of cyclosporine A (0.0865%), ethanol (0.1%), MYS-40 (2%), HPMC (0.3 w/v %), sodium dihydrogen phosphate (0.2 w/v %), and disodium EDTA (0.01% w/v %), sodium chloride to adjust the tonicity to 287 mOsm, and water.

Composition KK is intended to mean that disclosed in US20010041671, incorporated by reference herein, as Formulation 1, on Table 1. Composition LL is that disclosed in US20010041671 as Formulation 3, except that the concentration of cyclosporine is reduced.

Composition KK: cyclosporine A (0.02%), sodium hyaluronate (0.05%), Tween 80 (0.05%), $Na_2HPO_4.12H_2O$ (0.08%), sorbitol (5.46%), purified water added to 100 mL, pH 7.0-7.4, and mosm/L=295-305.

Composition LL: cyclosporine A (0.2%), sodium hyaluronate (0.10%), Tween 80 (5.00%), $Na_2HPO_4.12H_2O$ (0.08%), sorbitol (5.16%), purified water added to 100 mL, pH 7.0-7.4, and mosm/L=295-305.

The following composition is intended to mean that disclosed in Example 2 of U.S. Pat. No. 5,951,971, incorporated herein by reference.

Composition MM: cyclosporine A (0.025 g), polyoxyl 40 stearate (0.5 g), hydroxypropyl methylcellulose (0.2 g), butylated hydroxytoluene (0.0005 g), ethanol (0.1 g), sodium chloride (0.73 g), sodium dihydrogen phosphate (0.2 g), sodium edetate (0.1 g), sodium hydroxide to adjust pH to 6.0, and water to make 100 mL.

In another embodiment the composition provides more cyclosporin A than Composition AA provides to the cornea of a female New Zealand white rabbit 30 minutes after topical ocular administration of one drop of said composition or Composition AA, wherein the drop of said composition and the drop of Composition AA are the same volume.

In another embodiment the composition provides more cyclosporin A than Composition BB provides to the cornea of a female New Zealand white rabbit 30 minutes after topical ocular administration of one drop of said composition or Composition BB, wherein the drop of said composition and the drop of Composition BB are the same volume.

In another embodiment the composition provides more cyclosporin A than Composition CC provides to the cornea of a female New Zealand white rabbit 30 minutes after topical ocular administration of one drop of said composition or Composition CC, wherein the drop of said composition and the drop of Composition CC are the same volume.

In another embodiment the composition provides more cyclosporin A than Composition DD provides to the cornea of a female New Zealand white rabbit 30 minutes after topical ocular administration of one drop of said composition or Composition DD, wherein the drop of said composition and the drop of Composition DD are the same volume.

In another embodiment the composition provides more cyclosporin A than Composition EE provides to the cornea of a female New Zealand white rabbit 30 minutes after topical ocular administration of one drop of said composition or Composition EE, wherein the drop of said composition and the drop of Composition EE are the same volume.

In another embodiment the composition provides more cyclosporin A than Composition FF provides to the cornea of a female New Zealand white rabbit 30 minutes after topical ocular administration of one drop of said composition or Composition FF, wherein the drop of said composition and the drop of composition FF are the same volume.

In another embodiment the composition provides more cyclosporin A than Composition GG provides to the cornea of a female New Zealand white rabbit 30 minutes after topical ocular administration of one drop of said composition or Composition GG, wherein the drop of said composition and the drop of composition GG are the same volume.

In another embodiment the composition provides more cyclosporin A than Composition HH provides to the cornea of a female New Zealand white rabbit 30 minutes after topical ocular administration of one drop of said composition or Composition HH, wherein the drop of said composition and the drop of composition HH are the same volume.

In another embodiment the composition provides more cyclosporin A than Composition II provides to the cornea of a female New Zealand white rabbit 30 minutes after topical ocular administration of one drop of said composition or Composition II, wherein the drop of said composition and the drop of composition II are the same volume.

In another embodiment the composition provides more cyclosporin A than Composition JJ provides to the cornea of a female New Zealand white rabbit 30 minutes after topical ocular administration of one drop of said composition or Composition JJ, wherein the drop of said composition and the drop of composition JJ are the same volume.

In another embodiment the composition provides more cyclosporin A than Composition KK provides to the cornea of a female New Zealand white rabbit 30 minutes after topical ocular administration of one drop of said composition or Composition KK, wherein the drop of said composition and the drop of composition KK are the same volume.

In another embodiment the composition provides more cyclosporin A than Composition LL provides to the cornea of a female New Zealand white rabbit 30 minutes after topical ocular administration of one drop of said composition or Composition LL, wherein the drop of said composition and the drop of composition LL are the same volume.

In another embodiment the composition provides more cyclosporin A than Composition MM provides to the cornea of a female New Zealand white rabbit 30 minutes after topical ocular administration of one drop of said composition or Composition MM, wherein the drop of said composition and the drop of composition MM are the same volume.

In another embodiment the composition provides more cyclosporin A than Composition AA provides to the conjunctiva of a female New Zealand white rabbit 30 minutes after topical ocular administration of one drop of said composition or Composition AA, wherein the drop of said composition and the drop of Composition AA are the same volume.

In another embodiment the composition provides more cyclosporin A than Composition BB provides to the conjunctiva of a female New Zealand white rabbit 30 minutes after topical ocular administration of one drop of said composition or Composition BB, wherein the drop of said composition and the drop of Composition BB are the same volume.

In another embodiment the composition provides more cyclosporin A than Composition CC provides to the conjunctiva of a female New Zealand white rabbit 30 minutes after topical ocular administration of one drop of said composition or Composition CC, wherein the drop of said composition and the drop of Composition CC are the same volume.

In another embodiment the composition provides more cyclosporin A than Composition DD provides to the conjunctiva of a female New Zealand white rabbit 30 minutes after topical ocular administration of one drop of said composition or Composition DD, wherein the drop of said composition and the drop of Composition DD are the same volume.

In another embodiment the composition provides more cyclosporin A than Composition EE provides to the conjunctiva of a female New Zealand white rabbit 30 minutes after topical ocular administration of one drop of said composition or Composition EE, wherein the drop of said composition and the drop of Composition EE are the same volume.

In another embodiment the composition provides more cyclosporin A than Composition FF provides to the conjunctiva of a female New Zealand white rabbit 30 minutes after topical ocular administration of one drop of said composition or Composition FF, wherein the drop of said composition and the drop of composition FF are the same volume.

In another embodiment the composition provides more cyclosporin A than Composition GG provides to the conjunctiva of a female New Zealand white rabbit 30 minutes after topical ocular administration of one drop of said composition or Composition GG, wherein the drop of said composition and the drop of composition GG are the same volume.

In another embodiment the composition provides more cyclosporin A than Composition HH provides to the conjunctiva of a female New Zealand white rabbit 30 minutes after topical ocular administration of one drop of said composition or Composition HH, wherein the drop of said composition and the drop of composition HH are the same volume.

In another embodiment the composition provides more cyclosporin A than Composition II provides to the conjunctiva of a female New Zealand white rabbit 30 minutes after topical ocular administration of one drop of said composition or Composition II, wherein the drop of said composition and the drop of composition II are the same volume.

In another embodiment the composition provides more cyclosporin A than Composition JJ provides to the conjunctiva of a female New Zealand white rabbit 30 minutes after topical ocular administration of one drop of said composition or Composition JJ, wherein the drop of said composition and the drop of composition JJ are the same volume.

In another embodiment the composition provides more cyclosporin A than Composition KK provides to the conjunctiva of a female New Zealand white rabbit 30 minutes after topical ocular administration of one drop of said composition or Composition KK, wherein the drop of said composition and the drop of composition KK are the same volume.

In another embodiment the composition provides more cyclosporin A than Composition LL provides to the conjunctiva of a female New Zealand white rabbit 30 minutes after topical ocular administration of one drop of said composition or Composition LL, wherein the drop of said composition and the drop of composition LL are the same volume.

In another embodiment the composition provides more cyclosporin A than Composition MM provides to the conjunctiva of a female New Zealand white rabbit 30 minutes after topical ocular administration of one drop of said composition or Composition MM, wherein the drop of said composition and the drop of composition MM are the same volume.

Comparison of two compositions in a person or animal can be carried out by, among other means, administering the claimed composition to one eye and the second composition to the second eye.

In another embodiment the composition provides more cyclosporin A than Composition AA provides to the cornea of a female New Zealand white rabbit over a period of 24 hours after topical ocular administration of one drop of said composition or Composition AA, wherein the drop of said composition and the drop of Composition AA are the same volume.

In another embodiment the composition provides more cyclosporin A than Composition BB provides to the cornea of a female New Zealand white rabbit over a period of 24 hours after topical ocular administration of one drop of said composition or Composition BB, wherein the drop of said composition and the drop of Composition BB are the same volume.

In another embodiment the composition provides more cyclosporin A than Composition CC provides to the cornea of a female New Zealand white rabbit over a period of 24 hours after topical ocular administration of one drop of said composition or Composition CC, wherein the drop of said composition and the drop of Composition CC are the same volume.

In another embodiment the composition provides more cyclosporin A than Composition DD provides to the cornea of a female New Zealand white rabbit over a period of 24 hours after topical ocular administration of one drop of said composition or Composition DD, wherein the drop of said composition and the drop of Composition DD are the same volume.

In another embodiment the composition provides more cyclosporin A than Composition EE provides to the cornea of a female New Zealand white rabbit over a period of 24 hours after topical ocular administration of one drop of said composition or Composition EE, wherein the drop of said composition and the drop of Composition EE are the same volume.

In another embodiment the composition provides more cyclosporin A than Composition FF provides to the cornea of a female New Zealand white rabbit over a period of 24 hours after topical ocular administration of one drop of said composition or Composition FF, wherein the drop of said composition and the drop of composition FF are the same volume.

In another embodiment the composition provides more cyclosporin A than Composition GG provides to the cornea of a female New Zealand white rabbit over a period of 24 hours after topical ocular administration of one drop of said composition or Composition GG, wherein the drop of said composition and the drop of composition GG are the same volume.

In another embodiment the composition provides more cyclosporin A than Composition HH provides to the cornea of a female New Zealand white rabbit over a period of 24 hours after topical ocular administration of one drop of said composition or Composition HH, wherein the drop of said composition and the drop of composition HH are the same volume.

In another embodiment the composition provides more cyclosporin A than Composition II provides to the cornea of a female New Zealand white rabbit over a period of 24 hours after topical ocular administration of one drop of said composition or Composition II, wherein the drop of said composition and the drop of composition II are the same volume.

In another embodiment the composition provides more cyclosporin A than Composition JJ provides to the cornea of a female New Zealand white rabbit over a period of 24 hours after topical ocular administration of one drop of said composition or Composition JJ, wherein the drop of said composition and the drop of composition JJ are the same volume.

In another embodiment the composition provides more cyclosporin A than Composition KK provides to the cornea of a female New Zealand white rabbit over a period of 24 hours after topical ocular administration of one drop of said composition or Composition KK, wherein the drop of said composition and the drop of composition KK are the same volume.

In another embodiment the composition provides more cyclosporin A than Composition LL provides to the cornea of a female New Zealand white rabbit over a period of 24 hours after topical ocular administration of one drop of said composition or Composition LL, wherein the drop of said composition and the drop of composition LL are the same volume.

In another embodiment the composition provides more cyclosporin A than Composition MM provides to the cornea of a female New Zealand white rabbit over a period of 24 hours after topical ocular administration of one drop of said composition or Composition MM, wherein the drop of said composition and the drop of composition MM are the same volume.

In another embodiment the composition provides more cyclosporin A than Composition AA provides to the conjunctiva of a female New Zealand white rabbit over a period of 24 hours after topical ocular administration of one drop of said composition or Composition AA, wherein the drop of said composition and the drop of Composition AA are the same volume.

In another embodiment the composition provides more cyclosporin A than Composition BB provides to the conjunctiva of a female New Zealand white rabbit over a period of 24 hours after topical ocular administration of one drop of said composition or Composition BB, wherein the drop of said composition and the drop of Composition BB are the same volume.

In another embodiment the composition provides more cyclosporin A than Composition CC provides to the conjunctiva of a female New Zealand white rabbit over a period of 24 hours after topical ocular administration of one drop of said composition or Composition CC, wherein the drop of said composition and the drop of Composition CC are the same volume.

In another embodiment the composition provides more cyclosporin A than Composition DD provides to the conjunctiva of a female New Zealand white rabbit over a period of 24 hours after topical ocular administration of one drop of said composition or Composition DD, wherein the drop of said composition and the drop of Composition DD are the same volume.

In another embodiment the composition provides more cyclosporin A than Composition EE provides to the conjunctiva of a female New Zealand white rabbit over a period of 24 hours after topical ocular administration of one drop of said composition or Composition EE, wherein the drop of said composition and the drop of Composition EE are the same volume.

In another embodiment the composition provides more cyclosporin A than Composition FF provides to the conjunctiva of a female New Zealand white rabbit over a period of 24 hours after topical ocular administration of one drop of said composition or Composition FF, wherein the drop of said composition and the drop of composition FF are the same volume.

In another embodiment the composition provides more cyclosporin A than Composition GG provides to the conjunctiva of a female New Zealand white rabbit over a period of 24 hours after topical ocular administration of one drop of said composition or Composition GG, wherein the drop of said composition and the drop of composition GG are the same volume.

In another embodiment the composition provides more cyclosporin A than Composition HH provides to the conjunctiva of a female New Zealand white rabbit over a period of 24 hours after topical ocular administration of one drop of said composition or Composition HH, wherein the drop of said composition and the drop of composition HH are the same volume.

In another embodiment the composition provides more cyclosporin A than Composition II provides to the conjunctiva of a female New Zealand white rabbit over a period of 24 hours after topical ocular administration of one drop of said composition or Composition II, wherein the drop of said composition and the drop of composition II are the same volume.

In another embodiment the composition provides more cyclosporin A than Composition JJ provides to the conjunctiva of a female New Zealand white rabbit over a period of 24 hours after topical ocular administration of one drop of said composition or Composition JJ, wherein the drop of said composition and the drop of composition JJ are the same volume.

In another embodiment the composition provides more cyclosporin A than Composition KK provides to the conjunctiva of a female New Zealand white rabbit over a period of 24 hours after topical ocular administration of one drop of said composition or Composition KK, wherein the drop of said composition and the drop of composition KK are the same volume.

In another embodiment the composition provides more cyclosporin A than Composition LL provides to the conjunctiva of a female New Zealand white rabbit over a period of 24 hours after topical ocular administration of one drop of said composition or Composition LL, wherein the drop of said composition and the drop of composition LL are the same volume.

In another embodiment the composition provides more cyclosporin A than Composition MM provides to the conjunctiva of a female New Zealand white rabbit over a period of 24 hours after topical ocular administration of one drop of said composition or Composition MM, wherein the drop of said composition and the drop of composition MM are the same volume.

In one embodiment, wherein topical administration of one 35 µL drop of said composition to each eye of a female New Zealand white rabbit provides to the corneas of said rabbit at least about 500 ng of cyclosporin A per gram of cornea of said rabbit at 30 minutes after said topical administration.

In another embodiment, topical administration of one 35 µL drop of said composition to each eye of a female New Zealand white rabbit provides to the corneas of said rabbit at least about 2000 ng of cyclosporin A per gram of cornea of said rabbit at 30 minutes after said topical administration.

In another embodiment, topical administration of one 35 µL drop of said composition to each eye of a female New Zealand white rabbit provides to the corneas of said rabbit at least about 2400 ng of cyclosporin A per gram of cornea of said rabbit at 30 minutes after said topical administration.

In another embodiment, topical administration of one 35 µL drop of said composition to each eye of a female New Zealand white rabbit provides to the corneas of said rabbit at least about 17000 ng of cyclosporin A per gram of cornea of said rabbit over a period of 24 hours after said topical administration.

In another embodiment, topical administration of one 35 µL drop of said composition to each eye of a female New Zealand white rabbit provides to the conjunctivas of said rabbit at least about 3300 ng of cyclosporin A per gram of conjunctiva of said rabbit over a period of 24 hours after said topical administration.

In another embodiment, said composition is an aqueous solution containing from 0.005% to about 0.04% cyclosporin A, wherein topical administration of one 35 µL drop of said composition to each eye of a New Zealand rabbit provides at least about 17000 ng of cyclosporin A per gram of cornea to the corneas of said rabbit as determined by:
  topically administering said composition to each eye of each of 15 female New Zealand white rabbit test subjects, and
  determining the amount of cyclosporin A in the corneas of three subjects at times of about 0.5 hours, about 2 hours, about 6 hours, about 12 hours, and about 24 after administration to said subject,
wherein the amount of cyclosporin A in the cornea is determined only once for each subject.

In another embodiment, said composition is an aqueous solution containing from 0.005% to about 0.04% cyclosporin A, wherein topical administration of one 35 µL drop of said composition to each eye of a New Zealand rabbit provides at least about 17000 ng of cyclosporin A per gram of conjunctiva to the conjunctivas of said rabbit as determined by:
  topically administering said composition to each eye of each of 15 female New Zealand white rabbit test subjects, and
  determining the amount of cyclosporin A in the conjunctivas of three subjects at times of about 0.5 hours, about 2 hours, about 6 hours, about 12 hours, and about 24 after administration to said subject,
wherein the amount of cyclosporin A in the conjunctiva is determined only a single time for each subject.

As mentioned above, these compositions are suitable for use in other mammals other than rabbits, including humans.

Thus, any composition in the claims or elsewhere which is characterized by in vivo rabbit bioavailability testing is contemplated for use in a person or in another mammal. Defining a composition in terms of bioavailability in rabbits should not be construed to limit a method of treatment using the composition to use on rabbits, but treatment with the composition should be construed to include treatment on humans and other mammals.

The foregoing description details specific methods and compositions that can be employed to practice the present invention, and represents the best mode contemplated. However, it is apparent for one of ordinary skill in the art that further compositions with the desired pharmacological properties can be prepared in an analogous manner. Thus, however detailed the foregoing may appear in text, it should not be construed as limiting the overall scope hereof; rather, the ambit of the present invention is to be governed only by the lawful construction of the claims.

What is claimed is:

1. An aqueous solution comprising cyclosporin A at a concentration of about 0.0001% (w/v), Polysorbate 80, glycerin, mannitol, carboxymethylcellulose sodium, and water, wherein the aqueous solution contains no oil.

2. The solution of claim 1, wherein the Polysorbate 80 is at a concentration of 1% (w/v), the glycerin is at a concentration of 1% (w/v), the mannitol is at a concentration of 0.5% (w/v), and the carboxymethylcellulose sodium is at a concentration of 0.5% (w/v).

3. The solution of claim 2, further comprising sodium citrate dihydrate, potassium chloride, boric acid, and sodium borate decahydrate.

4. A method comprising topically administering a composition according to claim 1 to an eye of a mammal in need thereof to enhance or restore lacrimal gland tearing.

5. The method of claim 4, wherein said method increases tear production in a tear-deficient eye.

6. The method of claim 4, wherein said method is effective in treating keratoconjunctivitis sicca.

7. The method of claim 4, wherein said method is effective in treating dry eye disease.

8. The method of claim 4 wherein the mammal is a human patient, and wherein less than 10% of human patients suffer burning or stinging when said composition is administered only once a day for a period of three months.

9. The method of claim 4 wherein the mammal is a human patient, and wherein less than 10% of human patients suffer ocular burning when said composition is administered only once a day for a period of three months.

10. The method of claim 4 wherein the composition is administered only once a day.

* * * * *